United States Patent
Chouinard et al.

(10) Patent No.: US 7,670,367 B1
(45) Date of Patent: *Mar. 2, 2010

(54) MULTI-SECTION FILAMENTARY ENDOLUMINAL STENT

(75) Inventors: Paul F. Chouinard, Maple Grove, MN (US); Patrick A. Haverkost, Brooklyn Center, MN (US); Christopher L. Thatcher, Blairstown, NJ (US); Margarita Falkovich, Paramus, NJ (US); Robert C. Thistle, Brockton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1846 days.

This patent is subject to a terminal disclaimer.

(21) Appl. No.: 10/130,585

(22) PCT Filed: Nov. 16, 2000

(86) PCT No.: PCT/US00/31500

§ 371 (c)(1),
(2), (4) Date: Feb. 3, 2003

(87) PCT Pub. No.: WO01/35864

PCT Pub. Date: May 25, 2001

Related U.S. Application Data

(63) Continuation-in-part of application No. 09/442,165, filed on Nov. 16, 1999, now Pat. No. 6,585,758.

(51) Int. Cl.
*A61F 2/06* (2006.01)
*A61M 29/00* (2006.01)

(52) U.S. Cl. ............................ 623/1.15; 606/198

(58) Field of Classification Search .......... 623/1.15; 606/198
See application file for complete search history.

(56) References Cited

U.S. PATENT DOCUMENTS 4,655,771 A    4/1987   Wallsten .................... 623/1

(Continued)

FOREIGN PATENT DOCUMENTS

EP    0 796 597    9/1997

(Continued)

OTHER PUBLICATIONS

International Search Report dated Mar. 30, 2001.

(Continued)

*Primary Examiner*—Vy Q Bui
(74) *Attorney, Agent, or Firm*—Brooks, Cameron & Huebsch, PLLC

(57) ABSTRACT

A multi-section filamentary stent comprises a braided section of a first set of filaments, connected to at least one wound section comprising a second set of one or more filaments having a repeating configuration with a bent portion. The stent may comprise a first section, having a braided first stent architecture with a first flexibility and a first radial force, and a second section, having a non-braided second stent architecture with a secoid flexibility less than the first flexibility and a second radial force greater than the first radial force, in which at least one continuous filament is integral to both the first and second sections. The stent may have a radially compressed configuration and a radially expanded configuraton, in which the first section has a first shortening ratio, and the second section has a second shortening ratio less than the first shortening ratio.

39 Claims, 19 Drawing Sheets

U.S. PATENT DOCUMENTS

| | | | | |
|---|---|---|---|---|
| 5,019,090 | A | 5/1991 | Pinchuk | 606/194 |
| 5,061,275 | A * | 10/1991 | Wallsten et al. | 623/1.22 |
| 5,135,536 | A | 8/1992 | Hillstead | 606/195 |
| 5,282,824 | A | 2/1994 | Gianturco | 606/198 |
| 5,292,331 | A | 3/1994 | Boneau | 606/198 |
| 5,354,308 | A | 10/1994 | Simon et al. | 606/198 |
| 5,383,892 | A | 1/1995 | Cardon et al. | 606/198 |
| 5,395,390 | A | 3/1995 | Simon et al. | 606/198 |
| 5,507,767 | A | 4/1996 | Maeda et al. | 606/198 |
| 5,540,712 | A | 7/1996 | Kleshinski et al. | 606/198 |
| 5,591,229 | A | 1/1997 | Parodi | 623/1 |
| 5,643,339 | A | 7/1997 | Kavteladze et al. | |
| 5,649,949 | A | 7/1997 | Wallace et al. | |
| 5,693,086 | A * | 12/1997 | Goicoechea et al. | 623/1.11 |
| 5,746,765 | A * | 5/1998 | Kleshinski et al. | 128/898 |
| 5,746,766 | A | 5/1998 | Edoga | |
| 5,755,778 | A | 5/1998 | Kleshinski | 623/1 |
| 5,776,162 | A | 7/1998 | Kleshinski | 606/198 |
| 5,800,515 | A | 9/1998 | Nadal et al. | 623/1 |
| 5,817,126 | A * | 10/1998 | Imran | 623/1.15 |
| 5,827,321 | A | 10/1998 | Roubin et al. | 606/195 |
| 5,938,697 | A | 8/1999 | Killion | |
| 6,059,822 | A | 5/2000 | Kanesaka et al. | |
| 6,143,016 | A * | 11/2000 | Bleam et al. | 606/198 |
| 6,146,403 | A | 11/2000 | St. Germain | |
| 6,179,867 | B1 | 1/2001 | Cox | |
| 6,344,056 | B1 | 2/2002 | Dehdashtian | |

FOREIGN PATENT DOCUMENTS

| | | |
|---|---|---|
| EP | 0 830 853 | 3/1998 |
| EP | 0 880 948 | 12/1998 |
| FR | 2 765 097 | 6/1997 |
| WO | WO 98/47447 | 10/1998 |
| WO | WO 99/44535 | 9/1999 |
| WO | WO 00/19943 | 4/2000 |
| WO | WO 00/28921 | 5/2000 |
| WO | WO 00/42947 | 7/2000 |

OTHER PUBLICATIONS

International Search Report, dated Mar. 30, 2001, of International application, PCT/US00/31500.

* cited by examiner

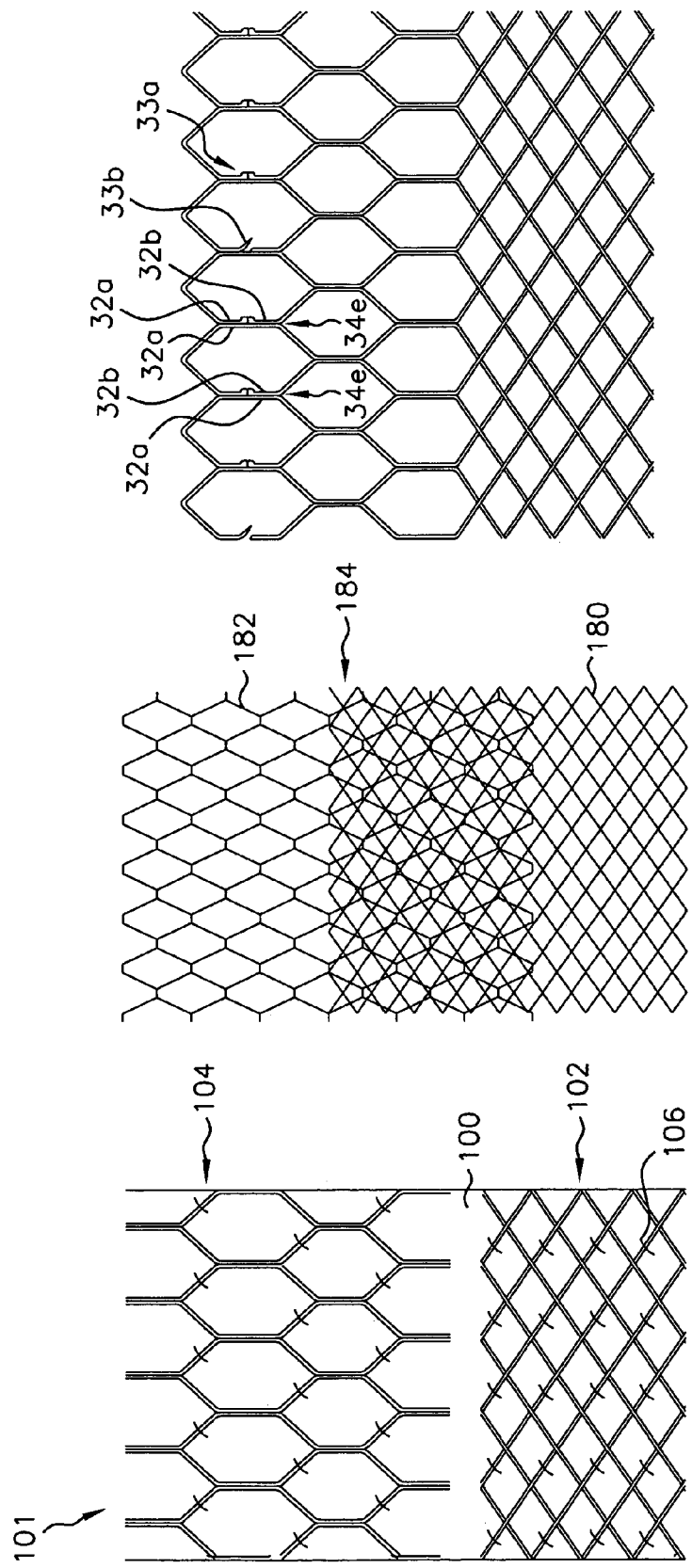

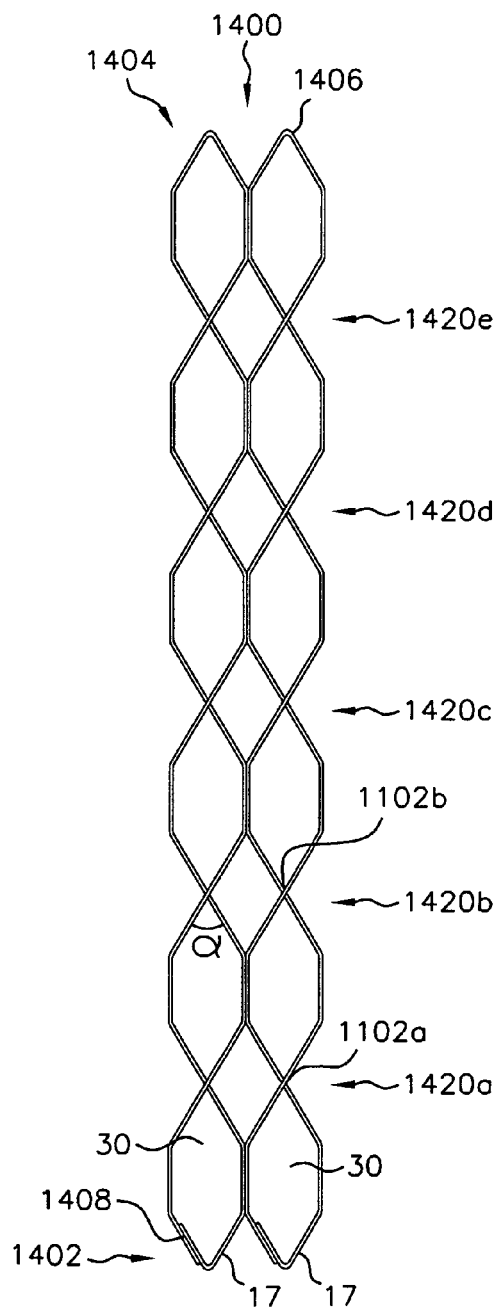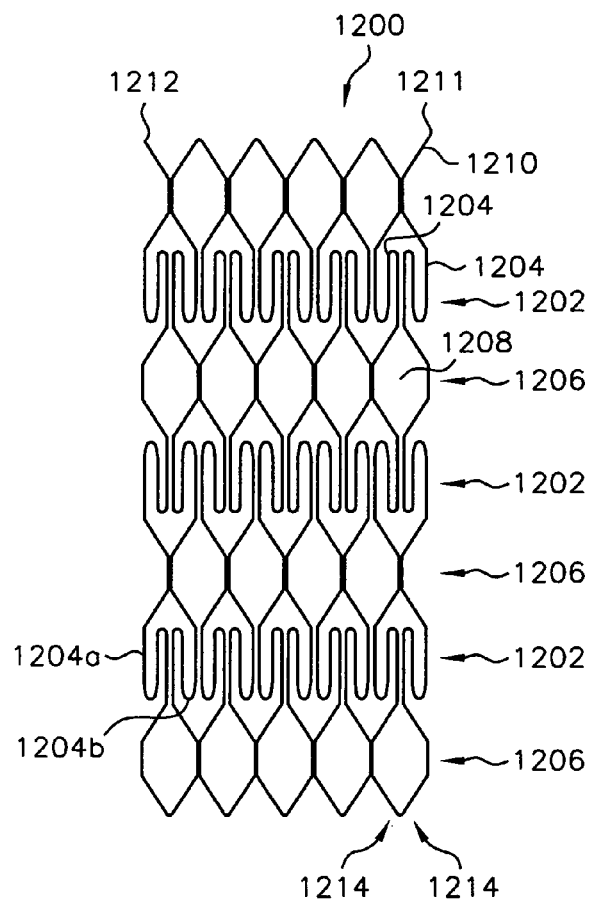
FIG. 26
FIG. 27

MULTI-SECTION FILAMENTARY ENDOLUMINAL STENT

CROSS-REFERENCE TO RELATED APPLICATIONS

This application claims priority from PCT Application Serial No. PCT/US00/31500, filed 16 Nov. 2000, which is a continuation-in-part of U.S. patent application Ser. No. 09/442,165 (status: pending), filed 16 Nov. 1999 now U.S. Pat. No. 6,585,758.

TECHNICAL FIELD

This invention relates generally to endoluminal stents, grafts, and/or prostheses and, more specifically, to stents comprising architectures that are hybrids of more than one architecture, including stents having multiple longitudinal sections of different stent architecture.

BACKGROUND OF THE INVENTION

A common method of treating vessel diseases such as stenoses, strictures, thrombosis, or aneurysms involves placing a stent into the affected vessel. Among other advantages, stents prevent vessels from collapsing, they reinforce vessel walls, they increase cross sectional area (and thereby volumetric flow), and they restore or maintain healthy blood flow. Many stents have been developed, and the prior art includes a wide variety of types and methods for their manufacture.

A stent is an elongated device used to support an intraluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft.

A prosthesis may be used, for example, to treat a vascular aneurysm by removing the pressure on a weakened part of an artery so as to reduce the risk of rupture. Typically, a prosthesis is implanted in a blood vessel at the site of a stenosis or aneurysm endoluminally, i.e. by so-called "minimally invasive techniques" in which the prosthesis, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the prosthesis to be ejected from the surrounding sheath or catheter in which it is restrained (or alternatively the surrounding sheath or catheter is retracted from the prosthesis), whereupon the prosthesis expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Various types of stent architectures are known in the art, including many designs comprising a filament or number of filaments, such as a wire or wires, wound or braided into a particular configuration. Included among these wire stent configurations are braided stents, such as is described in U.S. Pat. No. 4,655,771 to Hans I. Wallsten and incorporated herein by reference, the '771 Wallsten patent being only one example of many variations of braided stents known in the art and thus not intended as a limitation of the invention described herein later. Braided stents tend to be very flexible, having the ability to be placed in tortuous anatomy and still maintain patency. This flexibility of braided stents make them particularly well-suited for treating aneurysms in the aorta, where often the lumen of the vessel becomes contorted and irregular both before and after placement of the stent.

Braided stents also have several disadvantages, however. One such disadvantage is that the radial strength on the end of the braided stent is typically substantially less than the radial strength in the middle of the stent. Insufficient radial strength on the stent ends can result in an incomplete seal or migration of the device after implantation. Although flaring the ends or covering the stent with a graft can enhance the radial strength of the ends, the radial strength may still be insufficient. Also, when a braided stent is placed around a curve so that the end of the stent terminates within the curve, tapering of the stent end can result. This can also result in poor end sealing and migration. This phenomenon is particularly prevalent in stents greater than 16 mm in diameter. Although such tapering can be minimized by optimizing braid characteristics such as for example, wire count, wire diameter, and end flare, this tapering effect is still of significant concern.

Braided stents are also typically self-expanding, and are not well-suited for balloon-expandable applications because of insufficient compressive strength. This is a disadvantage, given a general physician preference for balloon expandable designs. Another disadvantage of such braided stent architectures is a tendency to shorten from a longer compressed length during introduction into the body to a shorter expanded length when deployed in a lumen.

Stents having zig-zag architecture are also known in the art. A zig-zag can be defined as a successive series of three struts connected by a pair of apex sections alternately pointing in opposite axial directions. Stents having such architecture are typically held together by connections at abutting apex sections. These connections may comprise sutures, welds, adhesive bonds, or any connection known in the art. The manufacturing process of making these numerous connections between abutting apex sections can be time consuming. Additionally, the connections may break, having potential clinical impacts. Also, the abutting apex sections tend to slide over each other when a compressive force is applied to the stent. Thus, there is a need for a zig-zag architecture which addresses some of these disadvantages.

A number of other stent architectures are known in the art that have greater compressive strength but less flexibility than braided stents. A stent architecture such as is shown and described in U.S. Pat. Nos. 5,354,308 and 5,395,390 to Simon et al., which is incorporated herein by reference, is an example of such a stent architecture. Such less flexible architectures are also not particularly well-suited for balloon-expandable applications. Thus, there is a need in the art for balloon-expandable stents having both flexibility and compressive strength.

Stent designs having greater radial strength but less flexibility than braided stents are also known in the art. Such stent designs can be combined with a braided stent design to produce a multi-segment stent having a flexible, braided stent member in the middle and less-flexible, higher-radial-strength stent members on the ends. Referring now to FIG. 18, one known way of combining such stents is merely to implant a braided stent 180 across a region to be repaired (not shown), and then to implant a higher-radial-strength stent 182 overlapping one or both ends 184 of the braided stent to more strongly anchor the braided stent to the lumen (not shown). Such a procedure, however, requires the implantation of multiple stents.

Referring now to FIGS. 1 and 2, it is also known, for example, to attach a braided stent member 2 to radially strong, rigid tubular stent end members 1 and 11. Braided stent member 2 comprises meshing wires 7 that criss-cross to form knots or overlaps 8. Wires 7 of braided stent member 2 are welded to flanges 6 of tubular stent end members 1 and 11 in pairs. This configuration is described in detail in U.S. Pat. No. 5,383,892 to Cardon et al. (hereinafter "Cardon").

In another configuration, described in detail in U.S. Pat. No. 5,817,126 to Imran, strands or ribbons of metal are attached to opposite ends comprising slotted metal stents. The strands or ribbons are then intertwined to form-a braided middle section.

The configuration disclosed in Cardon and Imran, however, while being applicable for providing a braided stent joined to a slotted metal stent, does not address joining a flexible, filamentary braided stent to a more rigid, wound filamentary stent. Filamentary stents of various winding configurations are well-known in the art, having various degrees of flexibility or rigidity. Inasmuch as such wound filamentary stents do not have discrete flanges as shown in FIGS. 1 and 2 and described in Cardon or flat areas of slotted metal for joining ribbons or strands as described in Imran, a wound filamentary stent cannot be joined to a braided filamentary stent as described in Cardon or Imran. It may also be desirable to provide more continuity between the end and middle sections than is offered by the mere welding of the ends of the wires or ribbons of the braided section to flanges or other elements of the slotted metal ends, such welding points potentially forming weak spots in the overall stent construction. Additionally, it may be desired to provide stents with variable radial strength sections having diameters larger than can be readily provided by slotted metal stents. In particular, it is desirable to provide multi-section stents wherein the flexible middle section and the more rigid end sections all comprise filamentary stents.

SUMMARY OF THE INVENTION

According to an embodiment of the invention, a multi-section filamentary stent comprises a braided section, which is a cylindrical mesh of a first set of filaments, and at least one wound section, which is connected to the braided section and which comprises a second set of one or more filaments in a repeating configuration having at least one bent portion. For example, a braided center section may be connected between two wound end sections. The repeating configuration of the second set of filaments in the wound section may comprise: a zig-zag configuration, an overlapping zig-zag configuration, a helical configuration, a non-helical configuration, or a configuration having polygonal cells. The polygonal cells may comprise hexagonal cells or overlapping hexagonal cells. At least one continuous filament may be a member of both the first set of filaments in the braided section and the second set of filaments in the wound section, serving to connect the two sections. In one exemplary configuration, at least one continuous filament may extend from the wound section into the braided section as a redundant filament, a tracer filament, or a redundant tracer filament.

The braided section is preferably connected to the wound section by virtue of at least one of the filaments being a member of both sets of filaments. The sections may also be connected to one another by sutures or welding, by a common graft providing a connection between the braided section and the wound section, or by one or more filaments of the braided section looped around apices of the wound sections, or by at least one filament of the wound section looping around at least one overlap in the braided section. At least a portion of the wound section may overlap and interlock with a portion of the braided section.

According to another embodiment of the invention, a multi-section filamentary stent comprises a first section, having a first stent architecture comprising one or more filaments in a first geometric configuration, and a second section, having a second stent architecture comprising one or more filaments in a second geometric configuration. The first stent architecture has a first flexibility and a first radial strength, and the second stent architecture has a second flexibility less than the first flexibility and a second radial strength greater than the first radial strength. The first stent architecture comprises a braided stent architecture. At least one continuous filament extends into both the first and second sections. The stent may comprise a middle section having the first stent architecture positioned between a distal end section and a proximal end section, each end section having the second stent architecture. The distal end section and the proximal end section may be identical or different in length and/or architecture. In particular, where the distal end is adapted to be positioned in a lumen upstream of the proximal end section relative to intraluminal fluid flow, the length of the distal end may be greater or the architecture may have a greater radial strength than the proximal end.

According to still another aspect of the invention, the stent comprises a first section having a first, braided stent architecture with a first shortening ratio, and a second section having a second stent architecture with a second shortening ratio. In a preferred embodiment, the first section is disposed as a middle section between two second sections disposed as end sections. The shortening ratio is the length of a section in its radially compressed configuration (typically longer) divided by its length in its radially expanded configuration (typically shorter). The first shortening ratio is greater than the second shortening ratio. The stent comprises at least one continuous filament contained in both the first and second sections.

The invention also comprises various forms of the stent, including a single stent adapted for individual delivery in a body lumen, two or more modular components adapted for joining together in situ in a non-branching lumen, and two or more modular components adapted for joining together in situ in a branching lumen.

A stent according to the present invention may also comprise a first section, having a first, braided stent architecture comprising one or more filaments in a first geometric configuration and having a first percentage of open area, and a second section, having a second stent architecture comprising one or more filaments in a second geometric configuration and having a second percentage of open area greater than the first percentage. The stent comprises at least one continuous filament contained in both the first and second sections. The first section of such a stent may be adapted for deployment in a first portion of a body lumen having no intersecting lumen connected thereto, whereas the second section is adapted for deployment in a second portion of the body lumen having one or more intersecting lumen connected thereto.

A stent according to the present invention may also comprise a first section having a first stent architecture comprising one or more filaments in a first geometric configuration, wherein the first stent architecture has a first radial strength and a known end effect comprising a reduction in radial strength along end lengths of the architecture. A second section of the stent, having a second stent architecture comprising one or more filaments in a second geometric configuration, has a radial strength substantially equal to the first radial strength or at least greater than the radial strength imparted by the end effect, and comprises an end section connected to the first section to counteract the end effect of the first stent architecture.

The present invention further comprises a stent comprising a plurality of zig-zag or sinusoidal members defined by a successive series of three struts connected to one another by a pair of adjacent apex sections pointing in opposite axial directions, at least a first zig-zag member overlaid upon a second zig-zag member and out of phase with the first zig-zag member to form an overlap between at least one strut of the first zig-zag member and one strut of the second zig-zag member. The stent may comprise at least two hoops comprising zig-zag or sinusoidal members and one or more cross-overs where a strut of an overlying hoop zig-zag crosses over a strut of an underlying hoop zig-zag that is in an opposite phase from the overlying hoop zig-zag. The lengths of the struts may be uniform throughout the stent or the length may vary according to a pattern. The stent may further comprise a plurality of axially aligned hoop pairs of underlying and overlying hoops, each hoop pair connected to an adjacent hoop pair by at least one abutting pair of apex sections that are connected to one another by a connecting member, such as a suture.

The invention comprises a stent having at least one section comprising a set of one or more filaments in a repeating configuration having at least one bent portion, wherein the repeating configuration defines at least a first hoop comprising hexagonal cells axially adjacent to a second hoop that does not comprise hexagonal cells. In a first embodiment, the second hoop may comprise a plurality of diamond-shaped cells and a plurality of overlaps. In a second embodiment, the second hoop may comprise a zig-zag architecture. Either embodiment may comprise an end winding in a zig-zag configuration, such as an overlapping zig-zag configuration with sets of double filaments extending parallel to one another or intersecting one another. In particular, the stent has a radially compressed configuration and a radially expanded configuration, and may be balloon-expandable from the radially compressed configuration to the radially expanded configuration.

The invention may also comprise a method of treating a body lumen, the method comprising implanting any of the stent structures described herein. In particular, the method may comprise introducing the stent into the body lumen in the compressed configuration and expanding the stent from the compressed configuration to the expanded configuration by inflating a balloon. The method may comprise the stent having diamond shaped cells and overlaps shortening by a lesser amount than an all-braided stent of the same length and axial overlap angle. Where the stent has at least one hoop of zig-zag architecture between a pair of hexagonal cell hoops, the method may further comprise the stent shortening by a lesser amount than a comparative stent having diamond-shaped cells and overlaps between the pair of hexagonal cell hoops.

It is to be understood that both the foregoing general description and the following detailed description are exemplary, but are not restrictive, of the invention.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 17 is an illustration of a multi-section stent embodiment according to the present invention wherein the wound stent section and a braided stent section are connected together by a common graft, where the tubular stent has been cut open along a line parallel to the stent axis and flattened.

FIG. 18 is an illustration of one end of a braided stent that is anchored by a higher-radial-strength stent overlapping the braided section as is known in the prior art, where both tubular stents have been cut open along a line parallel to the stent axis and flattened.

FIG. 19 is an illustration of a portion of a stent embodiment of the present invention showing the ends of certain filaments bent into protruding anchors.

FIG. 26 is an illustration of a portion of an exemplary stent comprising an overlapping polygonal cell architecture from end to end, where the tubular stent has been cut open along a line parallel to the stent axis and flattened, each filament extends from the bottom to the top and back to the bottom, and the axial overlap angle is less than 90°.

FIG. 27 is an illustration of an exemplary stent comprising a hybrid polygonal cell and zig-zag architecture having an odd number of zig-zag hoops, where the tubular stent has been cut open along a line parallel to the stent axis and flattened.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Figure 1:
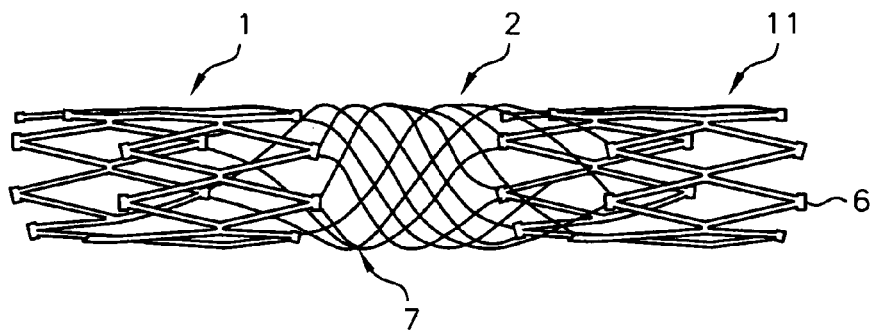
FIG. 1 is a perspective view of a multi-section stent embodiment known in the art.
Figure 2:
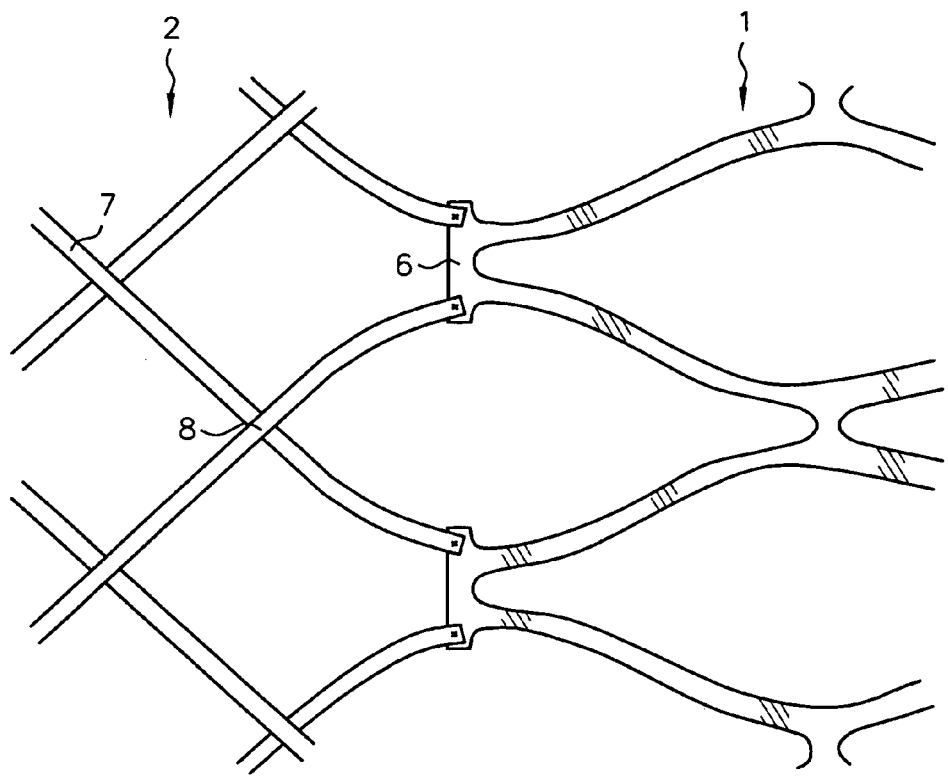
FIG. 2 is an enlarged view of a transition portion between the braided stent architecture section and the laser-cut architecture section of the stent embodiment of FIG. 1.
Figure 3:
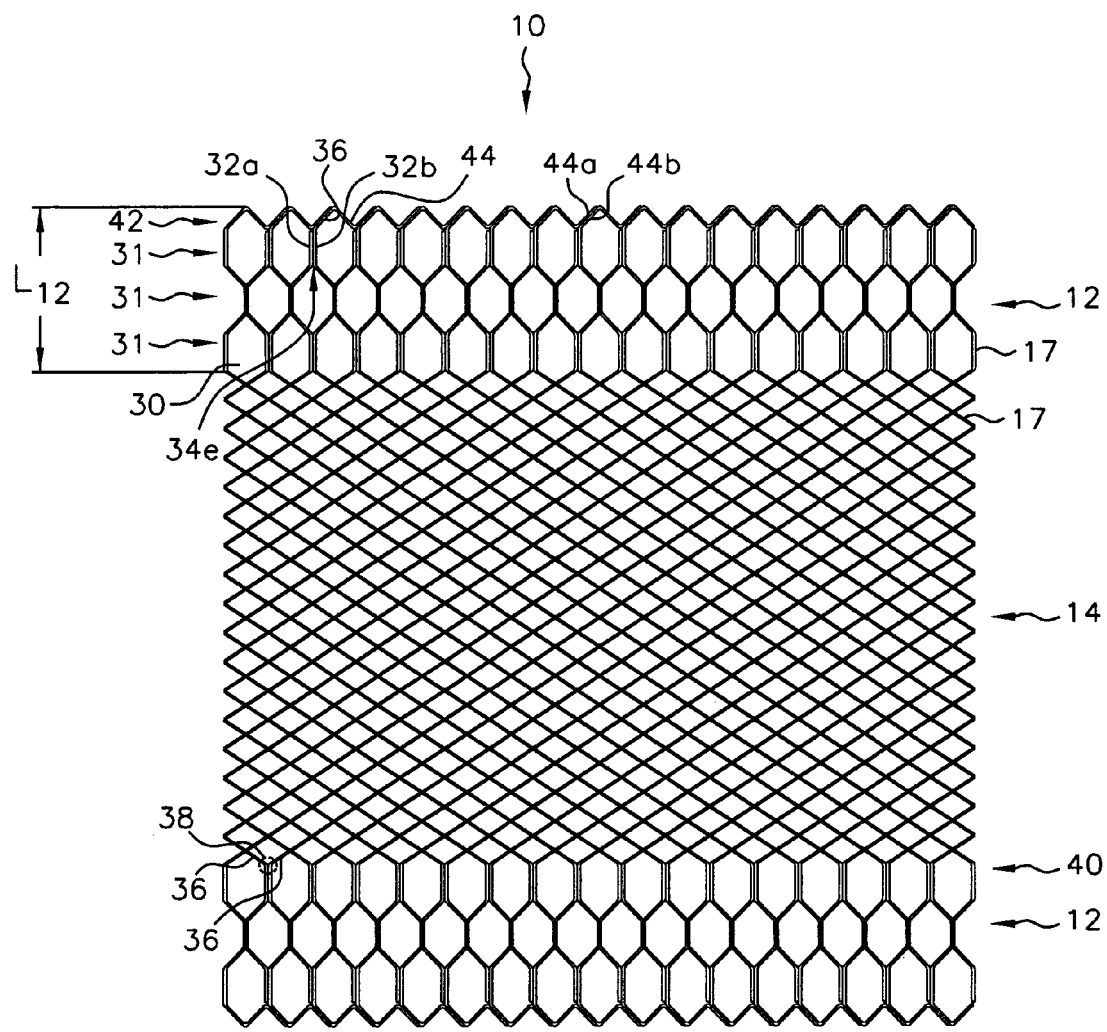
FIG. 3 is an illustration of a stent according to the present invention where the tubular stent has been cut open along a line parallel to the stent axis and flattened.

FIG. 3 shows an exemplary stent embodiment according to the present invention wherein the tubular stent has been cut along a line parallel to the tubular stent axis and flattened. As shown in FIG. 3, stent 10 comprises two end sections 12 and a middle section 14. Middle section 14 has a first stent architecture that comprises a braided stent such as is described in U.S. Pat. No. 4,655,771 to Hans I. Wallsten, and incorporated herein by reference, and end sections 12 have a second stent architecture that comprises a wound stent. End sections 12 have a wound stent architecture comprising one or more filaments in a repeating configuration having at least one bent portion. As shown in FIG. 3, the architecture of wound section 12 is substantially similar to the architectures described in U.S. Pat. Nos. 5,354,308 and 5,395,390 to Simon et al., which are incorporated herein by reference, and described further below. The structures described in the '771 Wallsten patent are merely examples of braided stent architecture, however, just as the structures disclosed in the '308 and '390 Simon patents are merely examples of particular wound stent architectures. None of the structures disclosed in the above named patents, however, are intended to be limiting, as any number of different stent architectures may be used to create multi-section stents in accordance with this invention, as is described in more detail below.

The braided middle section 14 as well as the wound end sections 12 comprise a plurality of filaments 17. Such filaments typically comprise metallic wire, such as nitinol, but may in the alternative comprise bioabsorbable or biostable polymers as are known in the art. The general use of the term "wire" herein is thus not intended as a limitation to metallic wire, but encompasses any type of filament.

Terminology Used Herein

Middle section 14 of stent 10, having the braided stent architecture, has a first flexibility and a first radial strength, and end sections 12, having the wound stent architecture, have a second flexibility less than the first flexibility and a second radial strength greater than the first radial strength. As used herein, "flexibility" or stiffness can be described in terms of the amount of force required to bend a stent into an arc. For example, referring to the schematic representation in FIGS. 4, the force f required to bend tubular stent 20 of a particular length into a given arc having a central angle and a given arc radius, is a measure of the stent flexibility. Thus, comparing two stents of equal length with different stent architectures, the stent requiring greater force to bend it into a given arc is relatively stiffer, whereas the stent requiring lesser force is relatively more flexible.

Figure 4:
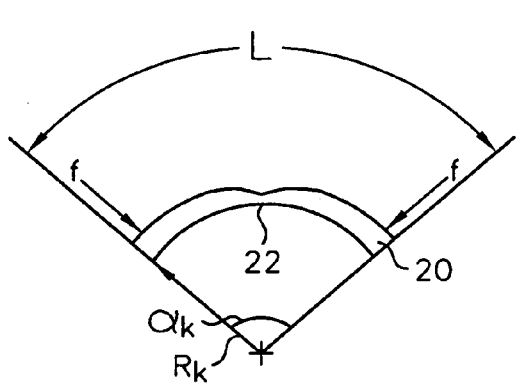
FIG. 4 is a schematic representation of a stent being flexed.

A measure of the "kink resistance" of a stent is the kink angle $\alpha_k$ or kink radius $R_k$ at which the stent kinks (i.e., when the tubular configuration becomes disrupted by crease 22 as shown in FIG. 4). Thus, if one compares the kink angle and kink radius of one tubular stent of a particular length and diameter having a first stent architecture to another tubular stent having the same length and diameter but a second stent architecture, the stent architecture having a lesser kink radius and a lesser kink angle has the most kink resistance. As is well known in the art, it is desirable to provide a stent which has good kink resistance, the extent to which is determined by the degree of tortuosity of the site where the stent will be deployed and, to a lesser extent, the degree of tortuosity of the path to the place of deployment.

As used herein, "radial strength" can be described generally as the resistance of a stent to radial compression. A stent with more radial strength exerts a greater outward radial force when compressed than does a stent with less radial strength. Thus, for example, a shape memory expandable or resiliently compressible stent may have a fully expanded diameter and a constrained diameter as deployed within a lumen. The fully expanded diameter is the diameter to which the stent would expand without any constraint. At the constrained diameter, the stent exerts a radial force F against the lumen, which when distributed over the surface area A of contact between the stent and the lumen can be expressed as a pressure P=F/A in force per unit area. Thus, radial strength can be expressed in terms of radial force or radial pressure. When comparing the radial strength of two stents having different stent architectures, if both stents have the same surface area A of contact (which is the same as having the same contact length where the diameters are equal), radial force may be one proper measure of radial strength. If one stent has a different surface area than the other, however, radial pressure is a more appropriate measure of radial strength. The radial strength and flexibility required depend primarily on the characteristics of the body lumen where the stent is to be deployed, and one skilled in the art can select a desired degree of stent radial strength and/or flexibility based on such characteristics.

Figure 5:
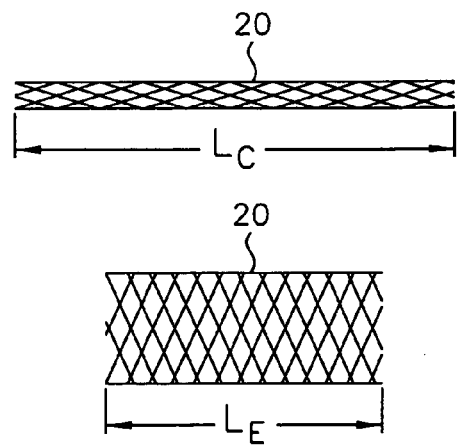
FIG. 5 is a schematic representation of a stent in its compressed state compared to its expanded state, illustrating the shortening of a stent during radial expansion.

As described in the background section, stents are typically inserted into a body lumen from a remote location through an insertion point in the body through which an "introducer", containing the stent in a radially compressed configuration, is threaded and navigated through the body lumen to the deployment location, where the stent is deployed in a radially expanded configuration. As referred to herein, "distal" refers to the direction further away from the insertion point and "proximal" refers to the direction closer to the insertion point. As shown in FIG. 5, stent 20 may have a first length $L_C$ when radially compressed and a second, shorter length $L_E$ when radially expanded. The "shortening ratio" $L_C/L_E$ can be used as a measure of this change in length. Braided stents typically have a relatively large shortening ratio as compared to standard wound stents. In general, it is desirable to reduce the shortening ratio to as close to 1 as possible in order to facilitate accurate deployment and to avoid stresses on a graft attached to the stent.

The specification and claims use the terms "stent architecture" and "geometric configuration" throughout. As used herein, "stent architecture" refers to all aspects of the stent construction, including geometric configuration, dimensions, and methods of formation. There are various categories of architecture, such as, wound stent architecture, braided stent architecture, laser cut tube stent architecture, filamentary stent architecture, polygonal cell stent architecture, or zig-zag stent architecture. A particular stent design may fall under several categories of stent architecture. For instance, one stent may comprise a filamentary, wound, polygonal cell stent architecture, whereas another stent may comprise a laser cut tube, polygonal cell stent architecture. "Filamentary" indicates that a stent comprises one or more filaments formed into the stent architecture, whereas a "laser cut tube" indicates that the stent comprises a tube that has been cut by a laser to form the geometric elements. Although there are numerous broad categories of stent architecture, within each broad category there are a number of stent architectures that are considered "different" for the purposes of this specification and claims. For example, one region of a stent having a certain height geometric element may be considered a first stent architecture whereas another region of the same stent having a similar geometric element of a different height may be considered a second, different stent architecture. Other differences in architecture from one region to another may include, for example, the number of elements in each hoop or the ratio of connected to unconnected elements between adjacent hoops.

As mentioned above, one component of stent architecture is geometric configuration. The "geometric configuration" refers to the geometric shape of the elements created within the stent. Thus, for instance, a stent having a filamentary, wound, polygonal cell stent architecture may have a geometric configuration wherein the cells are hexagonal and have a first size. Another stent having hexagonal cells of a second size still has the same geometric configuration as the stent having the hexagonal cells of the first size, but has a different stent architecture. As described herein, a stent section comprising filaments in a repeating configuration having at least one bent portion describes any of the filamentary and non-braided stents (such as those disclosed in this application) having some repeating configuration with a bent portion (i.e., either a curve or bend where the filament deviates from a linear direction as viewed when the stent is cut along its length and laid flat).

Wound/Braided Stent Hybrids

Returning now to FIG. 3, stent 10 comprises an embodiment wherein all filaments 17 are continuous filaments that extend from the wound end sections 12 into the braided middle section 14. Thus, end sections 12 and middle section 14 both have the same number of filaments, wherein the middle section consists only of filaments which also extend into the end section. In another embodiment, shown in FIG. 6, wound section 112 has a different number of filaments 17 than braided section 114. Thus, braided section 114 comprises a plurality of filaments 18 that do not extend into wound section 112. The continuous filaments extending from wound section 112 into braided section 114 may be redundant and/or tracer filaments 117. As referred to herein, a "redundant" filament or wire denotes a wire or filament that runs adjacent to another filament for some length of that element, wherein the filament to which the redundant filament runs adjacent is referred to as being an "integral" filament to the stent architecture. Thus, for instance, in FIG. 6, filaments 117 are redundant to the integral filaments 118 of the braided stent architecture of section 114. The term "tracer" is used to describe radiopaque (RO) marker filaments having a different degree of radiopacity than the surrounding filaments such that it is readily identifiable by fluoroscopic techniques. Such tracer filaments are typically redundant filaments. Although filament 117 may be a tracer filament, it may simply be a redundant, non-tracer filament. Similarly, it is possible to use any other filament, including an integral filament, such as filament 118, as a tracer filament.

Figure 6:
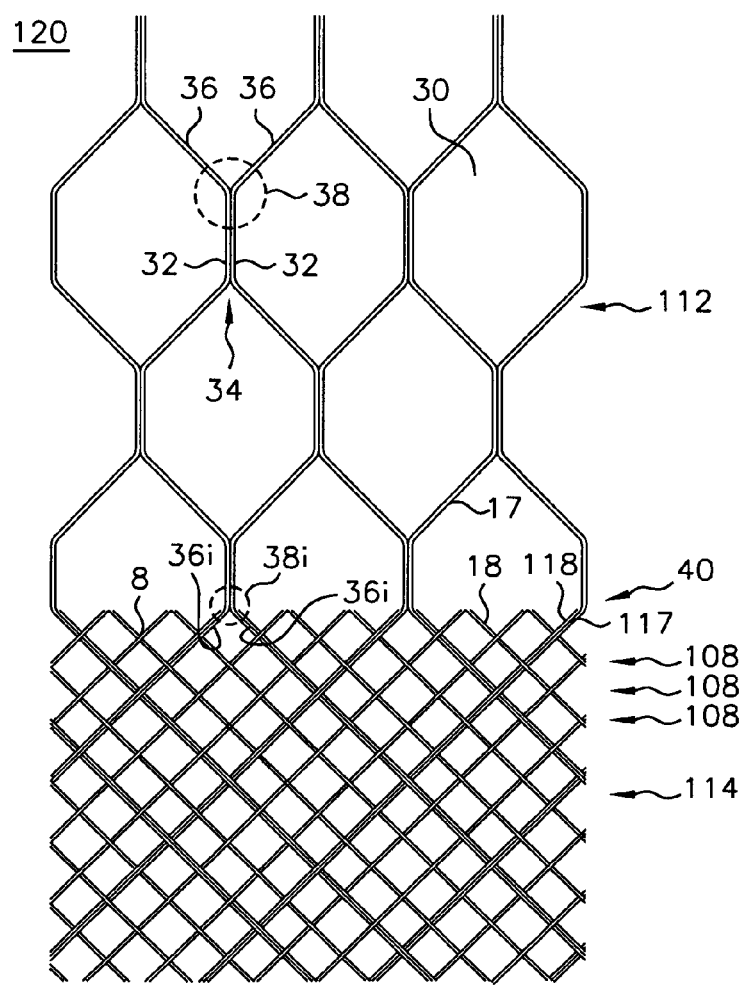
FIG. 6 is an illustration of a portion of a transition region between a polygonal cell stent section and a braided stent section where the tubular stent has been cut open along a line parallel to the stent axis and flattened.

FIG. 6 shows only the transition portion between braided section 114 and wound section 112 of a multi-section stent 120. Wound end section 112 may be at one end of stent 120 and braided section 114 may be in the middle, similar to the general layout shown in FIG. 3. In the alternative, stent 120 may have the braided and wound stent architectures at other locations within the overall stent configuration, as necessitated by the application. Furthermore, wherein a redundant filament (such as filaments 117) originates from a first stent architecture and extends into a second stent architecture, it may extend completely through both stent architectures, or only into a portion of the second architecture. For instance, such filaments may extend from a wound section 112 on one end of stent 120 as shown in FIG. 6, all the way through braided section 114, and emerge from the braided section to form a second wound section (not shown) on the other end of stent 120. In the alternative, such filaments may extend only partially from the first into the second architecture, such as extending only a limited number of rows 108 of overlaps 8 into braided section 114. Thus, for instance, braided section 114 of stent 120 as shown in FIG. 6 may extend for some distance beyond the portion of the stent shown in FIG. 6 whereas redundant filaments 117 may terminate at the length shown or at any length less than the full length of braided section 114.

As shown in FIG. 6, wound section 112 comprises a stent architecture having a plurality of polygonal, hexagonal cells 30 having as sides thereof straight axially-extending portions 32 joined together along a set of parallel lengths 34, the parallel lengths deviating from one another proximally and distally of each parallel length into diagonal lengths 36, such that each set of parallel lengths and attached diagonal lengths form a Y-shaped intersection 38. As shown in FIG. 6, the polygonal cell stent architecture in wound section 112 terminates at set of parallel lengths 34, which may be joined together by twisting them together, welding, suturing, or any means known in the art. In another embodiment, such as is shown in FIG. 3 and described herein later, the polygonal cell architecture may terminate in a zig-zag end winding. Yet another exemplary termination embodiment for a polygonal cell architecture is shown in FIG. 19.

As shown in FIG. 6, the diagonal lengths $36_i$ of each Y-shaped intersection $38_i$ at interface 40 between the wound section 112 and the braided section 114 extend from the wound section and are interwoven into the braided section as redundant filaments 117. Although not shown in FIG. 6, such filaments could also form part of the integral structure of the braided section 114, thus forming a connection between the two sections. As used herein, "integral" means necessary (non-redundant). For example, as shown in FIG. 3, the diagonal lengths 36 of each Y-shaped intersection 38 at interface 40 between wound end section 12 and braided middle section 14 extend into the wound section such that the braided section consists only of such filaments extended from the wound section. Thus, each filament 17 in each wound end section 12 continues into braided middle section 14 as a non-redundant filament 17 meshed into the braided stent architecture.

Multi-section stent embodiments in accordance with this invention having continuous wire filaments extending across the multiple sections (i.e. from the wound to the braided sections) have certain advantages, including that no further connection is required between the two stent sections. The continuous wires also provide a smooth transition between regions, rather than a sharp transition, thereby minimizing kinking. The smooth transition spreads out any strain, such as due to bending at the interface, over a continuous section of wire, rather than concentrating strain at, for instance, a weld point. Embodiments comprising only continuous wires that are integral to both the wound and braided section (such as is illustrated in FIG. 3) eliminate any loose ends that might otherwise become unraveled or pulled out of the braided configuration and/or protrude from the braided configuration in a way that can snag the body lumen or the graft.

The polygonal cell architecture shown in wound section 112 of stent 120 shown in FIG. 6 is particularly well suited for applications in which it is desired to be able to expand the stent from the compressed to the expanded configuration without a substantial degree of twist, meaning that there is no substantial change in the twisting of the stent between the radially compressed and expanded configurations. Because the polygonal cell architecture is a non-helical winding, there is substantially no inherent twisting of the stent structure between the compressed and expanded configurations. Similarly, the braided stent architecture has substantially no inherent twist as each filament oriented in one helical direction has another equivalent filament oriented in the opposite helical direction. The absence of twist is referred to herein as having no "substantial" twist because, although the braided stent and polygonal cell architectures discussed herein are not intended to have twist, some negligible but potentially measurable amount of twist may be present due to tension during the winding process or other factors. Thus, "substantially" no twist means that any twist is minimized to be essentially negligible and that there is no twist arising from stent geometry, only residual stress as may be imparted in the manufacturing process, for example.

Figure 7:
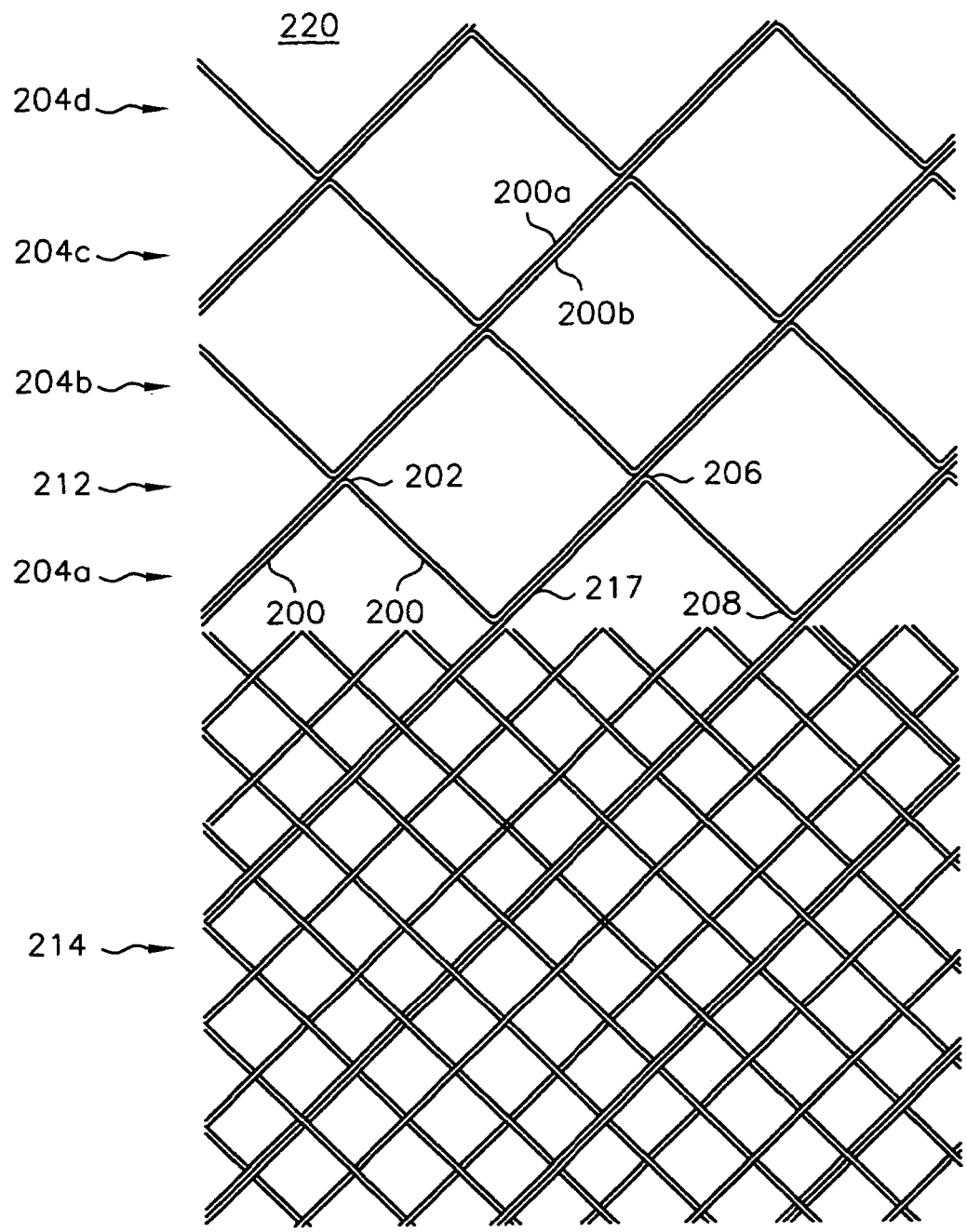
FIG. 7 is an illustration of a portion of a transition region between a zig-zag stent section and a braided stent section where the tubular stent has been cut open along a line parallel to the stent axis and flattened.

In an alternate embodiment, shown in FIG. 7, stent 220 comprises a first section 214 that has a braided stent architecture connected to a second section 212 comprising a helically wound zig-zag stent architecture. The zig-zag stent architecture comprises a plurality of struts 200 joined at apex sections 202, with a plurality of alternating oppositely-pointed apex sections arranged into hoops 204a, 204b, 204c, and 204d. Apex sections 202 pointing in a first direction can be referred to peaks 206 and apex sections pointing in the opposite direction can be referred to as a valleys 208, with any circumferentially adjacent, oppositely pointing apex sections together with three adjacent struts 200 forming a zig-zag. As shown in FIG. 7, each filament 217 of wound second section 212 extends into braided first section 214 as a redundant filament, which may be a tracer. In wound second section 212, each filament makes one full zig-zag in first hoop 204a and then extends into axially adjacent hoop 204b where it makes another full zig-zag before extending into to hoop 204c, and so on. Where one filament lies adjacent to another along struts 200a and 200b of adjacent apex sections 202a and 202b, the filaments may be joined together, such as by twisting them together, welding, suturing, brazing, or any means known in the art. Although four hoops 204a-d are shown in FIG. 7, any number of hoops may be constructed, as required by the application. Similarly, each filament may make more than one zig-zag before moving to the next hoop, may extend axially such that each filament skips one or more hoops before making the next zig-zag, may cross over another filament of an off-phase zig-zag, and/or may lie adjacent to another filament for a greater distance than just one strut. Thus, the zig-zag architecture shown in FIG. 7 is merely one exemplary zig-zag embodiment, but is not intended to limit the invention thereto.

Figure 8:
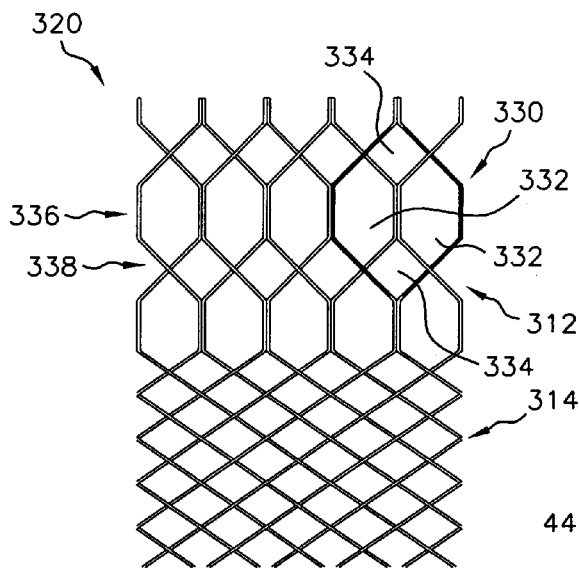
FIG. 8 is an illustration of a portion of a transition region between an overlapping polygonal cell stent section and a braided stent section where the tubular stent has been cut open along a line parallel to the stent axis and flattened.
Figure 10:
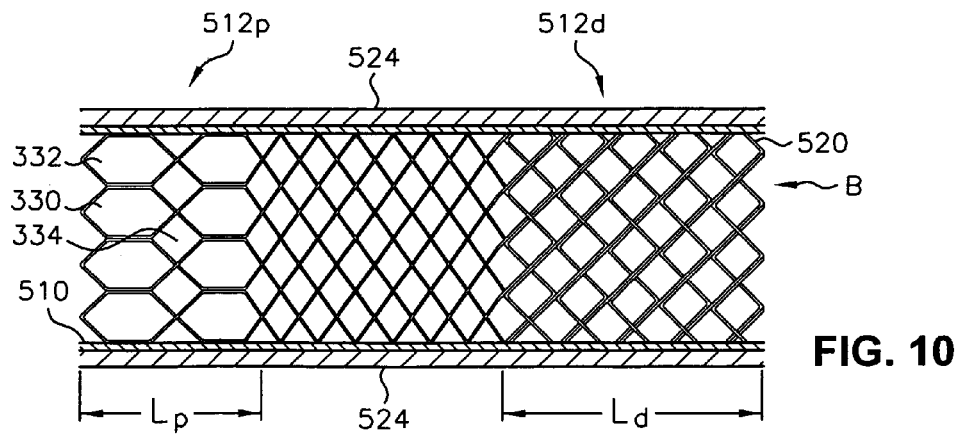
FIG. 10 is an illustration of an exemplary embodiment of a stent and attached graft implanted within a lumen according to the present invention, the stent having different stent architectures and lengths in its distal and proximal wound sections, with the lumen and graft shown in cross-section.

In another embodiment, shown in FIG. 8, the polygonal cells 330 in wound section 312 of stent 320 may overlap one another. The large overlapping hexagonal polygonal cells 330 (one of which is outlined in black for illustration) thus circumferentially bisect each other into four sub-cells—two hexagonal sub-cells 332 and two diamond-shaped sub-cells 334 to create rows 336 (or hoops when in tubular form) of hexagons alternating with rows 338 of diamonds. Although shown in FIG. 8 wherein braided section 314 does not comprise redundant filaments, an alternate embodiment may be constructed with redundant filaments. The overlapping cell architecture may be further modified by adding a zig-zag end winding, such as end winding 42 as shown in FIG. 3. Depending where the end winding is positioned axially, however, the resulting wound section may have only partial or full large hexagonal cells 330 and greater or fewer rows 336 of hexagonal sub-cells 332 or rows 338 of diamond sub-cells 334 than as shown in FIG. 8. For example, section 512p in FIG. 10 illustrates such an overlapping call architecture having a zig-zag end winding, where only partial large hexagonal cells 330 are present, resulting in a single row of diamond-shaped sub-cells 334 between two rows of hexagonal sub-cells 332. Additional embodiments comprising overlapping hexagonal architecture are discussed herein below under a separate subheading.

Thus, according to the present invention, the wound section, which generally has a greater radial strength and lesser flexibility than the braided section, may, for example, comprise one or more of: a zig-zag configuration, an overlapping zig-zag configuration, a helical configuration, a non-helical configuration, or a configuration having polygonal cells. The polygonal cells may comprise, for example, hexagonal cells or overlapping hexagonal cells. These geometric configurations are not limiting, however, as any filamentary stent architecture comprising any geometric configuration known in the art may be used. The filaments or wires that comprise the braided section may comprise only filaments that extend into and are integral to the wound section, or the braided section may have additional filaments that do not extend into the wound section. The filaments from the wound section may extend into the braided section as non-redundant elements of the braided section, or may extend into the braided section as redundant filaments. One or more wound sections may comprise end sections so connected to braided sections, or the wound or braided sections may be located anywhere along the length of the stent.

Within the various combinations and permutations of known stent architecture variables, any number of embodiments are possible. The length and/or architecture of the wound section can be tailored to each application to provide the radial strength desired. The several embodiments shown in FIGS. 3 and 6-9 and/or described below, therefore, are only exemplary and are not intended to be limiting. Thus, for example wound section 112 as shown in FIG. 6 consisting of polygonal cells 30 with no zig-zag end winding may be combined with braided section 14 as shown in FIG. 3. In such case, diagonals 36 extending from Y-shaped intersection 38 at interface 40 of the wound stent architecture 112 as shown in FIG. 6 extend into braided stent architecture 14 as non-redundant elements of the braided stent architecture 14 as shown in FIG. 3, rather than as redundant elements as shown in FIG. 6. Furthermore, the combination of stent architectures is not limited to only two types of architectures, such as one wound section connected to one braided section, or even three different stent architectures, such as a braided section connected to a polygonal cell section with a zig-zag end winding, but rather may comprise any number of different architectures in combination as needed to meet the needs of the specific application.

The many permutations include a stent comprising a wound section 212 having a zig-zag stent architecture such as is shown in FIG. 7, except that filaments 217 extend from wound section 212 into braided section 214 as non-redundant filaments such as is shown in FIG. 3, rather than as redundant filaments as shown in FIG. 7. Thus, a braided section 14 as shown in FIG. 3 may consist only of filaments 17 that extend between and are integral to both the braided section 14 and a zig-zag wound section similar to section 212 shown in FIG. 7.

End Windings

Returning now to FIG. 3, wound end section 12 is a hybrid between the polygonal cell stent architecture and the zig-zag architecture. As shown in FIG. 3, wound end section 12 comprises three rows 31 of hexagonal cells 30 and terminates in an end winding 42 that comprises a zig-zag structure. As such, one of the straight axially-extending portions 32a in the end set of parallel segments 34e terminates at the end of the set of parallel segments, whereas the other straight axially-extending portion 32b continues onward to form a diagonal 36 which then forms a zig-zag 44. Where struts of zig-zags 44a and 44b originating from adjacent polygonal cells 30 extend parallel adjacent one another, they may be joined together, such as by twisting them together, welding, suturing, or by any means known in the art. The zig-zag end winding may comprise more than one row of zig-zags, as desired. Also, rather than being an end winding, the zig-zag structure may be intermediate a braided section and a polygonal cell section, or may be one of any number of sections having different architecture within a single, continuous stent embodiment.

A zig-zag end winding 42 may be particularly advantageous as compared to terminating wound end section 12 at set of parallel lengths 34 as shown in FIG. 6, in that the zig-zag end winding provides greater radial strength, rounds the ends, and eliminates any wires axially protruding from the end of stent 10. Thus, a zig-zag end winding 42 coupled with an embodiment without redundant filaments, such as is shown in FIG. 3, optimally minimizes any such protruding wires from the stent. The minimization of protruding wires helps to minimize potential snagging of the stent during loading and deployment of the stent and minimizes the potential for puncturing or irritating the lumen wall with the sharp, protruding wires. Minimization of protruding wires also facilitates retracting and repositioning the stent after partial deployment.

Although zig-zag end winding 42 minimizes axially protruding wires, in some applications it may be desired to provide protruding wires as anchoring hooks to help maintain the position of a stent once it is deployed in a body lumen. For example, one such end winding style, shown in FIG. 19, comprises one axially-extending portion 32a of set of parallel lengths 34e defining the end periphery of cell 30 and abutting an axially-extending portion 32b of an adjacent set of parallel lengths. The ends of portions 32a and 32b may merely be turned in toward the center of cell 30 and clipped substantially in line with the set of parallel lengths 34e (so that there are no protruding ends) as shown at termination 33a, or one of the portions, such as 32a, may instead be bent into a protruding termination 33b in the form of an anchor or hook that protrudes circumferentially from the stent. Such an anchor 33b helps to anchor the stent into the wall of the lumen (not shown) into which the stent is implanted, as is known in the art. An end winding may comprise a mixture of both the non-protruding terminations 33a and protruding terminations 33b, for example, in a pattern such as having one protruding termination after every 3 non-protruding terminations, as shown in FIG. 19.

Figure 9:
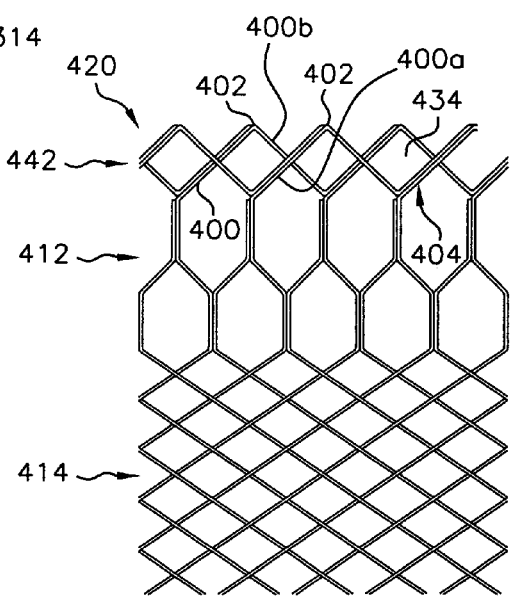
FIG. 9 is an illustration of a portion of a transition region between a hybrid polygonal cell/overlapping zig-zag stent section and a braided stent section where the tubular stent has been cut open along a line parallel to the stent axis and flattened, and the overlapping zig-zag end winding comprises sets of double filaments that are parallel to one another.

As shown in FIG. 9, stent 420 may comprise a wound section 412 comprising a hybrid polygonal cell and zig-zag architecture wherein the zig-zag end winding 442 is an overlapping zig-zag structure. In an overlapping zig-zag structure, as shown in FIG. 9, adjacent zig-zags circumferentially bisect one another, such that each strut 400a of a first zig-zag approaching an apex section 402 pointed in one direction crosses over another strut 400b of a second zig-zag coming from a circumferentially-adjacent apex section 402 pointed in the same direction, creating a row of diamond-shaped cells 434. In any of the hybrid hexagonal cell/zig-zag or hexagonal cell/overlapping zig-zag structures, the number of rows of hexagonal cells to zig-zag or overlapping zig-zag rows may be varied, with an equal number of rows of each type or more rows of one type than the other. A zig-zag and overlapping zig-zag architecture could also be combined. Although shown in FIG. 9 wherein braided section 414 does not comprise redundant filaments, an alternate embodiment may be constructed with redundant filaments.

Figure 21:
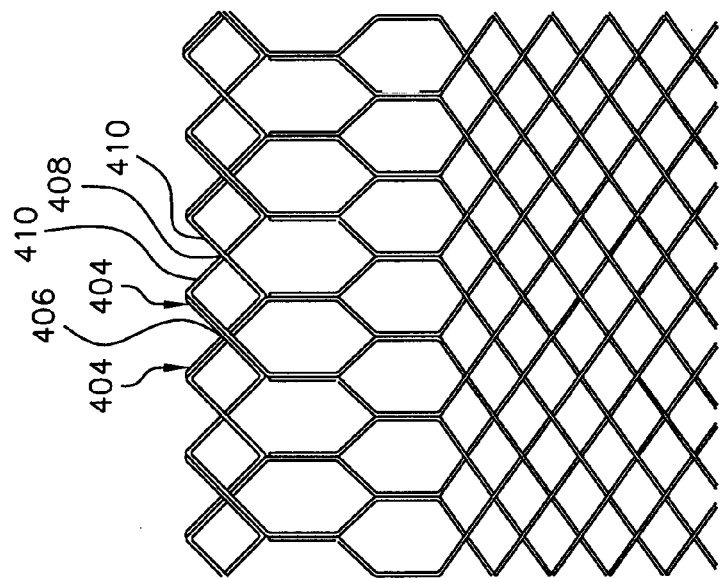
FIG. 21 is an illustration of a portion of a transition region between a hybrid polygonal cell/overlapping zig-zag stent section and a braided stent section where the tubular stent has been cut open along a line parallel to the stent axis and flattened, and the overlapping zig-zag end winding comprises sets of double filaments that intersect one another.

The overlapping zig-zag structure shown in FIG. 9 provides sets of double filaments 404 extending parallel to one another. Such a configuration may impart a twisting force upon expansion of the stent, which may be undesirable for certain applications. Therefore, to minimize any twisting forces, another embodiment of the overlapping zig-zag structure, shown in FIG. 21, may be constructed. As shown in FIG. 21, the overlapping zig-zag structure is similar to that shown in FIG. 9, except that the double filaments 404 cross over one another, providing a pattern consisting of sets 406 of crossed double filaments 404 alternating with sets 408 of crossed single filaments 410. As such, for each set of double filaments oriented in one direction, there is a set of double filaments oriented in the opposite direction such that any twisting forces are counteracted. Overlapping zig-zag architecture has benefits beyond merely as an end winding, however, and additional embodiments are discussed herein below under a separate sub-heading.

Different Architectures on Opposite Ends of the Stent

Although stent 10 depicted in FIG. 3 having wound end sections 12 and a braided middle section 14 shows identical end sections 12 having equal lengths $L_{12}$, an equal number of rows of polygonal cells 30, and the same stent architecture, a stent may also be constructed wherein each wound end section is different. For example, as shown in FIG. 10, because stent 520 is implanted with its distal end section 512d upstream from proximal end section 512p relative to blood flow along arrow B inside lumen 524, it is often desirable to have an especially effective seal between the graft covering 510 of stent 520 and the walls of lumen 524 to prevent blood from seeping between the graft and the lumen. A key factor in the effectiveness of the seal is the radial strength exerted by distal end section 512d against lumen 524. Because the dynamic pressure exerted by the blood flow attempting to seep between graft 510 and lumen 524 is strongest at the distal end section 512d, a higher overall radial strength may be required at the distal end section 512d than at the proximal end section 512p. Thus, stent 520 may have a different stent architecture (for example, a zig-zag end winding) in the distal end section than at the proximal end section, or the end sections may have the same stent architecture with a longer length $L_d$ of the distal end section than length $L_p$ of the proximal end section. As shown in FIG. 10, wound section 512d has a different architecture than section 512p and a length $L_d$ that is longer than length $L_p$. In an alternative embodiment, a stent may have a wound end section only on one end, for example the upstream end, and no wound section at the opposite end.

Modular and Bifurcated Modular Stents

Figures 11, 12:
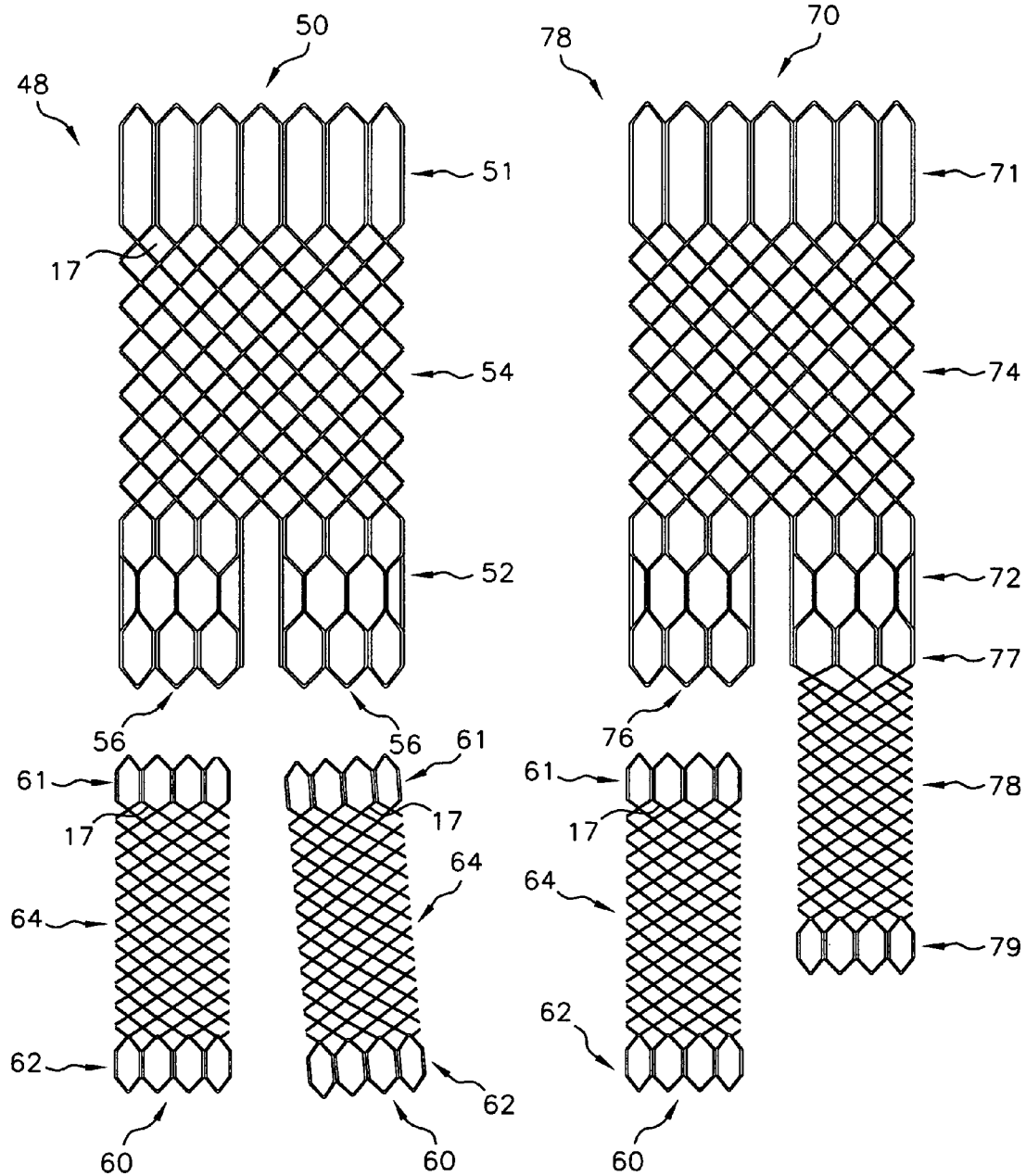
FIG. 11 is a side view illustration of a three-piece modular bifurcated stent according to the present invention.
FIG. 12 is a side view illustration of a two-piece modular bifurcated stent according to the present invention.

The various multi-section stents as described herein may be particularly well-suited to the construction of modular stents adapted for assembly in situ. Such modular stents comprise at least two modular components. For example, as shown in FIG. 11, modular stents are frequently used in applications directed for implantation in branching lumen, such as for repairing aneurysms of the aorta in the section of the aorta which branches into the right and left iliac arteries. Non-bifurcated modular stents are used in non-branching lumen. Thus, although discussed herein with respect to the bifurcated stent shown in FIG. 11, multi-section stents of the present invention may be applied to non-bifurcated modular stents as well.

As shown in FIG. 11, modular stent 48 comprises trunk component 50 and at least one modular leg component 60. Trunk component 50 further comprises a multi-section stent of the present invention in which there is a braided middle section 54 and a wound distal end section 51 and wound proximal end section 52. The wound proximal end section 52 of trunk component 50 is bifurcated into two connection sockets 56. Each leg component 60 similarly comprises a braided middle section 64 and a wound distal end section 61 and wound proximal end section 62. Thus, the braided middle sections of both components have a greater flexibility than the wound end sections, and the wound end sections have a greater radial strength than the braided middle section. In accordance with the present invention, each component 50 and 60 has at least one continuous filament 17 integral to both the braided and wound sections. As each component also has a radially compressed configuration and a radially expanded configuration, the braided stent architecture generally tends to have a shortening ratio that is greater than the shortening ratio of the wound stent architecture. Leg component 60 is adapted to be fitted together with trunk component 50 such that distal end sections 61 of the leg component interlocks inside proximal end section 52 of the trunk component into one of the sockets 56.

Bifurcated stent embodiments of the present invention may resemble stent 48 shown in FIG. 11, wherein there are two leg components 60 that each interlock inside the connection sockets 56 of the proximal end section 52 of the trunk component, or may resemble stent 78 as shown in FIG. 12. Stent 78 comprises a trunk component 70 having a distal end section 71, a trunk middle section 74 connected to the trunk distal end section 71, a trunk bifurcated section 72 connected to the trunk middle section and branching into a contralateral socket 76 and an integral leg transition 77. The integral leg transition is connected to an integral leg middle section 78 which is connected to an integral leg proximal end section 79. Modular leg component 60 of stent 78 is similar to the modular leg component described for stent 48 as shown in FIG. 11. Instead of having two modular legs as shown in FIG. 11, however, stent 78 has only a single leg 60 that connects into contralateral socket 76 of trunk component 70.

The use of multi-section stents of the present invention in bifurcated applications has certain advantages over bifurcated stents having other configurations. For example, bifurcated stents are typically used to treat aortic aneurysms and thus often incorporate a graft covering. Because of the large shortening ratio common to braided stent designs, the use of braided stents having graft coverings requires graft coverings that can accommodate shortening. Although such accommodating graft coverings are known, the use of braided stents in a bifurcated region, such as trunk bifurcated section 72, creates a complex geometry that complicates the pairing of graft to stent. Furthermore, the process for creating bifurcated regions using a braided stent may also be somewhat more complex than that for creating such a region using a wound stent. Thus, any complexities of using a braided architecture in a bifurcated region may be avoided by the use of a wound stent architecture in the bifurcated region of such a stent.

Additionally, because the present invention enables tailoring of different sections of a stent for different radial strength and flexibility, two- or three-piece bifurcated designs such as are shown in FIGS. 11 and 12 can be designed with a relatively short trunk section socket. The relatively short socket length is possible because the overall radial force needed to create a seal where the modular leg overlaps the inside of the trunk section socket can be distributed over a smaller surface area of contact using a higher radial strength stent section. Overlapping sections tend to be less flexible than non-overlapping sections, and may be subject to kinking. Thus, potential kinking due to overlapping stents sections can be reduced via minimizing the length of the overlapping section. A shorter socket length enables a shorter overall trunk length and longer, more flexible leg sections.

Although the modular stent embodiments shown in FIGS. 11 and 12 comprise wound end sections (i.e. sections 51, 56, 61, and 62 in FIG. 11 and sections 61, 62, 71, 72 and 79 in FIG. 12) with a common stent architecture, or at least a common geometric configuration, and middle sections (i.e. sections 54 and 64 in FIG. 11 and sections 54, 75, and 78 in FIG. 12) having a common braided architecture, each individual section may have a different stent architecture, including a different geometric configuration.

Alternate Means for Joining Braided and Wound Sections

Figure 13:
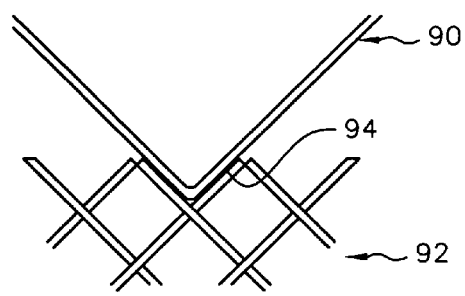
FIG. 13 is an illustration of a portion of a transition region between a zig-zag stent section and a braided stent section showing a weld joining the two different stent sections.
Figure 14:
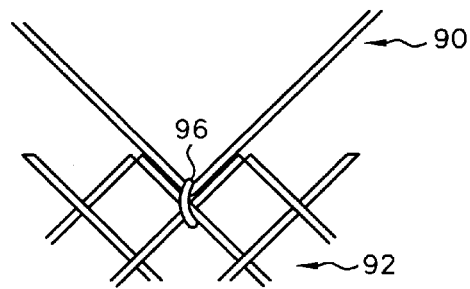
FIG. 14 is an illustration of a portion of a transition region between a zig-zag stent section and a braided stent section showing a suture joining the two different stent sections.

Several embodiments of wound filament stent architectures joined with braided filament stent architectures have been described above wherein each embodiment included a continuous filament which extends between both the wound and braided architectures for connecting the two stent sections. Other joining means can also be provided. FIGS. 13-16 show portions of different embodiments of an exemplary transition region between a zig-zag stent architecture section 90 and a braided stent architecture section 92. As shown in FIG. 13, braided section 92 may be connected to the wound section 90 by a weld 94. Instead, as shown in FIG. 14, braided section 92 and wound section 90 may be connected by a suture 96.

Figure 15:
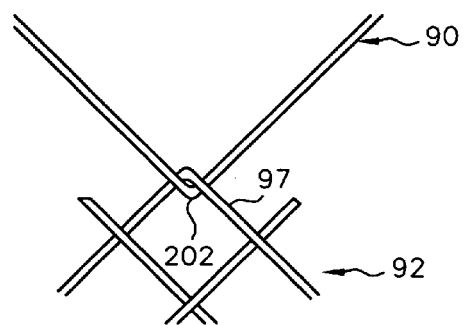
FIG. 15 is an illustration of a portion of a transition region between a zig-zag stent section and a braided stent section showing a filament of the braided section looping around an apex section of the zig-zag section to join the two sections.
Figure 16:
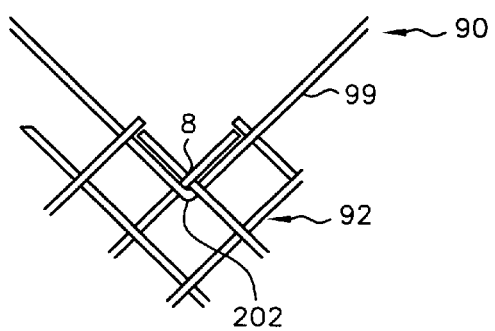
FIG. 16 is an illustration of a portion of a transition region between a zig-zag stent section and a braided stent section showing a filament of zig-zag section looping around an overlap in the braided section to join the two sections.

In another embodiment, as shown in FIG. 15, a filament 97 of braided section 92 may be looped around an apex section 202. Filament 97 may be a continuous filament that is interwoven into braided section 92, or two filaments welded together where the filaments meet after looping through apex section 202. Filament 97 may be interwoven through the entire length of braided section 92 as a redundant or non-redundant member, or may extend through only a portion of the braided section 92 as a redundant member. Rather than a filament of the braided section looping through the wound section, a filament 99 which forms apex section 202 of wound section 90 may be looped around an overlap 8 in braided section 92, as shown in FIG. 16. Additionally, any of the configurations shown in FIGS. 13-16 may be combined.

As shown in FIG. 17, where stent 101 comprises a common graft 100 attached to both braided section 102 and wound section 104 of the stent, the common graft may provide the connection between the braided section and the wound section. Graft 100 may be connected to stent 101 by, for example, sutures 106 as shown in FIG. 17, or by staples, adhesive bonds, or any means known in the art. Stent 101 and attached graft 100 shown in FIG. 17 are illustrated with the tubular stent/graft combination cut along a line parallel to the stent axis and flattened, with the stent shown overlying the graft. Graft 100 may be an outer covering for stent 101, in which case FIG. 17 shows an internal view, or graft 100 may be an inner liner for stent 101, in which case FIG. 17 shows an external view.

Applications and Advantages of Hybrid Braided/Wound Stents

Although the use of stents generally is widespread in endovascular applications where the stent is deployed in a blood vessel, this invention may also be beneficial for applications in other body lumen. The advantages inherent in this invention, which combines the flexibility found in braided stent architectures with the secure anchoring force and stent-end patency provided by wound stent architectures, are particularly well-suited for applications in any tortuous lumen. Thus, for instance, this invention may be advantageous for use in enteral applications that require flexibility to conform to a tortuous intestine but that also require strong anchoring forces to hold the stent in place. Additionally, the treatment of ostial lesions, such as in bilary or renal applications, where strong anchoring and radial strength is particularly needed at the end of the stent, may also benefit from this invention. Therefore, this invention is applicable to a broad range of stent diameters, from femoral applications in the 6 mm range and iliac applications in the 8 mm range, to aortic trunk applications in the 34 mm range and thoracic applications in the 45 mm range.

Although described herein with respect to certain specialized embodiments, such as embodiments for treating abdominal aortic aneurysms (AAA) or for providing greater radial strength at the ends of a stent for anchoring, the present invention may be applied across a broad range of applications. An important advantage offered by this invention, is that it allows controlled tailoring of the radial strength of a particular portion of a stent as necessary to meet an application. Therefore, although providing ends with greater strength may be one application, the invention may be used to provide controlled radial strength in any portion of the stent, including to provide lesser strength in certain sections if desired. For example, referring now to FIG. 22, to facilitate the conformance of a stent 700 to one or more known tortuous regions 702 in a lumen 704 into which the stent is to be implanted, the stent may be designed with one or more relatively flexible sections, such as braided section 706 as compared to wound sections 708, to align with the tortuous region. Wound sections 708 are not necessarily end sections, and thus stent 700 may further comprise other flexible regions therein, for example, to accommodate other tortuous regions of lumen 704.

In yet another embodiment, the invention may be used to provide the same degree of radial strength across the entire length of a stent, rather than to provide an increased or decreased radial strength in some portion. For example, a wound end section on a braided stent may be provided to counteract a lesser radial strength that would otherwise be present at the ends of a particular stent architecture. For example, braided stents have a known end effect wherein the radial strength at the ends of the braided architecture is less than in the middle. This problem is sometimes addressed by flaring the braided ends (so that when compressed to the same diameter as the rest of the stent, the radial force exerted is the same). In accordance with this invention, however, a wound end section may be provided at the end of the braided section to provide the same degree of radial strength across the entire length of the stent, or at least a greater degree of radial strength in the end section than would otherwise be present due to the end effect. Such a wound end section may or may not be flared. Such a stent may have a superficial appearance similar stent embodiments described and illustrated herein, such as, for example, stent 10 as shown in FIG. 3, but having fewer rows 31 of cells 30 and no end winding 42, such that the radial strength of end 12 is only sufficient to counteract the end effect of braided section 14, but not to provide greater strength than the remainder of the stent.

Figure 20:
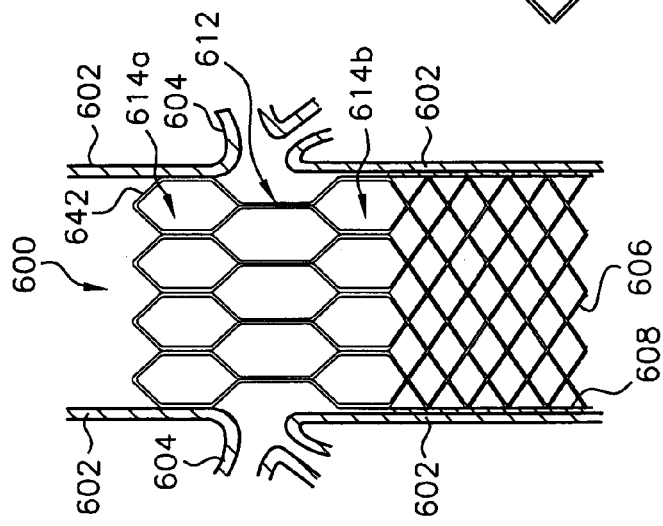
FIG. 20 is a cross-sectional illustration of a portion of a stent embodiment of the present invention shown implanted in an aorta bridging the renal arteries.

The unlimited combinations of different filamentary stent architectures in accordance with the present invention may be beneficial not just because such combinations enable control of the radial force at various points along the length of the stent, but also because such combinations may provide other structural advantages. For example, referring now to FIG. 20, there is shown an embodiment wherein a stent 600 is implanted in a region of an aorta 602 adjacent intersecting renal lumen 604. Although braided section 606, which may have a graft covering 608, is desirable for its flexibility below and above renal lumen 604, the dense, close-knit structure of the braided section, having a first percentage of open area, would block blood flow into the renal lumen if it extended across them, even without covering 608. In fact, in some cases, lumen of lesser physiological importance than renal lumen 604 (for example, capillaries that provide redundant vascular pathways to areas that can be served by other pathways) are intentionally covered in the process of treating an aneurysm or other problem in the main lumen with a graft-lined or covered stent. To prevent covering "important" intersecting lumen (lumen that cannot be covered without potentially serious impact to the patient) such as lumen 604, wound section 612, having a polygonal geometry with a second percentage of open area greater than the first percentage, is provided in the portion of the stent implanted adjacent renal lumen 604. As shown in FIG. 20, wound section 612 has an even greater percentage of open area than sections 614a and 614b of polygonal architecture above and below it, respectively. Section 612, as shown in FIG. 20, comprises a geometric configuration that is elongated, but essentially similar, to sections 614a and 614b. Section 614a also comprises a zig-zag end winding 642. The polygonal stent structure having a greater percentage of open area provides negligible obstruction of blood flow into the renal lumen. Although greater radial strength may be provided in polygonal architecture section 612 as compared to braided section 606, section 612, because of its elongated shape, has a lesser radial strength than sections 614a and 614b. In certain applications such differences in radial strength may not be necessary or desired, but rather the greater percentage of open area in the stent architecture adjacent the renal branches may be the advantageous difference sought between the sections of different architecture.

"Percentage of open area" as used herein may be defined as:

$$\frac{A_s - \sum A_{fp}}{A_s} = \frac{(\pi D_s L_s - \sum D_f L_f)}{\pi D_s L_s}$$

where:
$A_S$=the cylindrical surface area of the stent ($\pi D_S L_S$)
$L_S$=the length of the stent portion at issue
$D_S$=the diameter of the stent
$\Sigma A_{fp}$=the "projected" rectangular area ($D_f L_f$) of each filament onto $A_S$
$D_f$=the diameter of the filament
$L_f$=the length of the filament contained within length Ls It should be noted that the projected area $A_{fp}$ is not the same as the actual surface area of each filament length $L_f$, which is equal to projected area $A_{fp}$ times $\pi$.

The methods of constructing the various braided and wound stent architectures are well known in the art. For example, the method for constructing the polygonal cell stent architecture is described in U.S. Pat. No. 5,540,712 to Kleshinski et al. and essentially comprises winding the stent around pins on a mandrel. The weaving of filaments together into a braid is a well-known operation, not just in the medical field, but also in textile manufacture. Combining the braided and wound architectures can be undertaken by providing first a braided stent by means known in the art and leaving loose filaments protruding from one or both ends. These loose filaments can then be wound around pins on a mandrel to make the wound section. In the alternative, a wound section can be first constructed and then the loose ends protruding from that section braided, and then optionally, the loose ends protruding from the braided section wound around a mandrel into another wound section. Where, for instance a bifurcated stent such as is shown in FIG. 12 is constructed, alternation between winding operations and braiding operations may occur numerous times until all the requisite sections have been completed to meet the application needs.

Although certain combinations of braided and wound stent architectures have been described extensively herein, other combinations of stent architectures, each having different flexibility, radial strength, or shortening characteristics may be combined in accordance with this invention. Furthermore, although polygonal cell and zig-zag wound stents have been described specifically herein, other wound stent constructions may also be acceptable for combination with braided stent architectures. For example, a wound stent architecture similar to that shown in sections 112 of FIG. 6 may be constructed with polygonal cells 30 rotated by 90 degrees such that parallel lengths 34 align circumferentially rather than axially. Also, wound stent architectures as described in the following U.S. Patents and patent families claiming priority therefrom may be well-suited for combination with braided stent designs by one or more of the methods described herein, the following list of U.S. Patents being only exemplary, not limiting:

U.S. Pat. No. 5,019,090 Pinchuk
U.S. Pat. No. 5,135,536 Hillstead
U.S. Pat. No. 5,292,331 Boneau
U.S. Pat. No. 5,282,824 Gianturco
U.S. Pat. No. 5,354,308 Simon et al.
U.S. Pat. No. 5,507,767 Maeda et al.
U.S. Pat. No. 5,800,515 Nadal et al.

Although a braided stent configuration is discussed herein extensively as an exemplary flexible architecture, other flexible stent architectures known in the art may also be used. Thus, generally, the present invention comprises a multi-section filamentary stent comprising a first section, having a first stent architecture comprising one or more filaments in a first geometric configuration, and a second section, having a second stent architecture comprising one or more filaments in a second geometric configuration. The first stent architecture has a first flexibility and a first radial strength, and the second stent architecture has a second flexibility less than the first flexibility and a second radial strength greater than the first radial strength. The stent comprises at least one continuous filament integral to both the first and second sections. The first geometric configuration is substantially different from the second geometric configuration. In another embodiment, the first and second stent architectures may differ in percentage of open area, but not necessarily differ in radial strength or flexibility. In yet another embodiment, the first and second stent architectures may have the same radial strength and flexibility wherein the second architecture merely compensates for an end effect in the first stent architecture that would otherwise provide a lesser radial strength at the end.

Overlapping Hexagonal Cell Architecture

The overlapping hexagonal cell architecture such as is shown in FIG. 8 has been found to be useful not only as an end winding for a hybrid wound and braided stent, but also an advantageous architecture to be used throughout a stent from end to end, as shown in FIGS. 23-26. This optimum architecture is particularly well-suited for balloon-expandable stent constructions when constructed of plastically deformable filaments. Plastically deformable materials include but are not limited to: stainless steel, gold, platinum, tantalum, titanium, tungsten, palladium, nickel alloys, titanium alloys, cobalt alloys, and combinations thereof. The overlapping hexagonal cell architecture can also be described as essentially a hybrid between the braided architecture as shown in the '771 patent and the cell architecture of the '308 and '390 patents. In overlapping hexagonal cell architecture, the braided and cell architectures alternate row by row, creating alternating rows of hexagonal cells 332 and diamond-shaped cells 334, each row of diamond-shaped cells 338 further comprising a plurality of cross-overs 1100 similar to those found in braided architecture. Overlapping hexagonal cell architecture provides improved flexibility as compared to the all-hexagonal cell architecture with reduced shortening as compared to an all-braided architecture.

Figure 23:
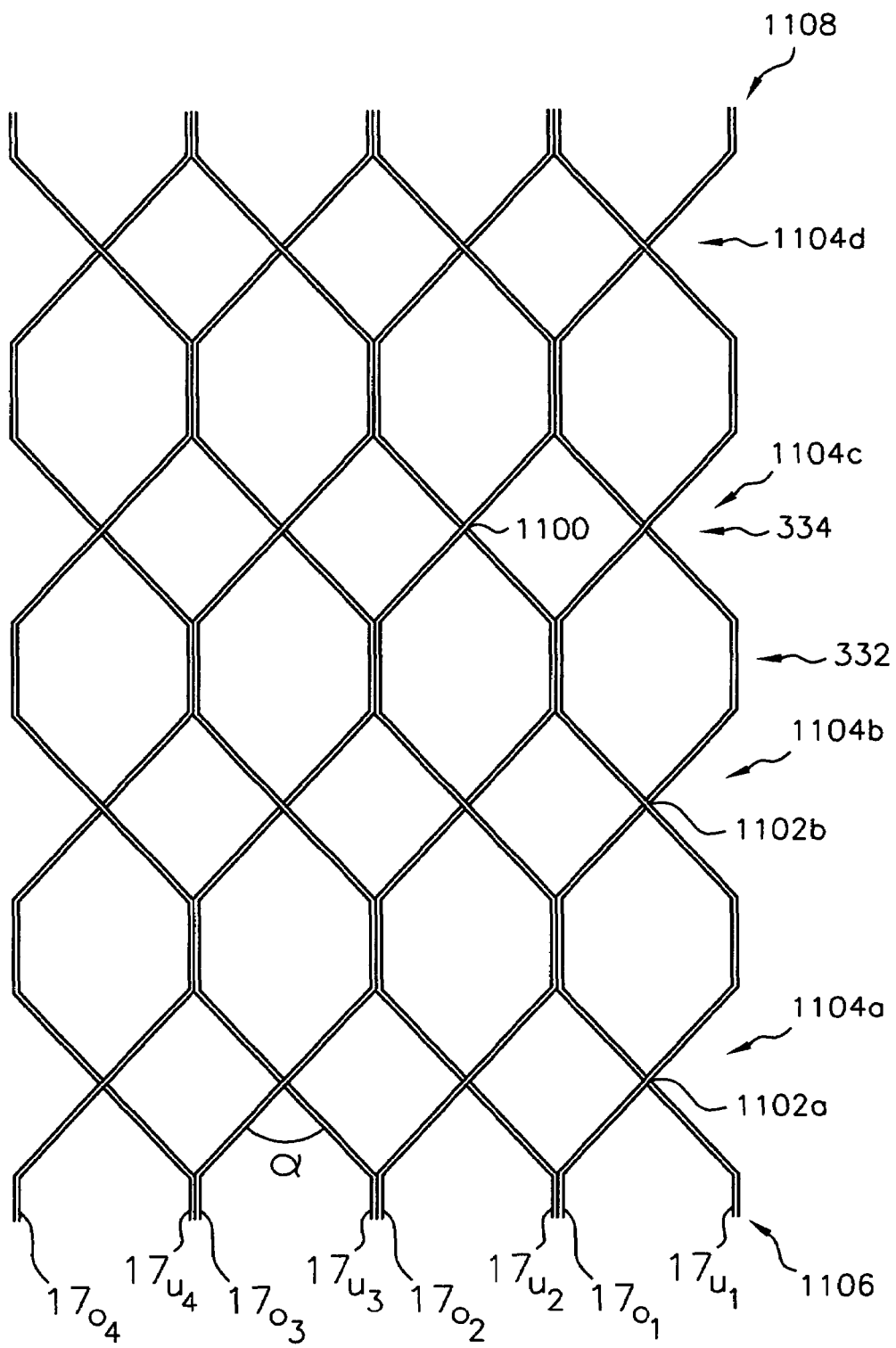
FIG. 23 is an illustration of a portion of an exemplary stent comprising an overlapping polygonal cell architecture from end to end, where the tubular stent has been cut open along a line parallel to the stent axis and flattened, and the under-over relationship of the overlaps are different from hoop to hoop.

The overlapping cell architecture may be created in any number of ways. As shown in FIG. 23, filaments $17u_{1-4}$ are all positioned underneath filaments $17o_{1-4}$ at overlaps 1102a and 1102b throughout stent 1100. Thus, the stent may be created by first winding all filaments $17u_x$ and then all filaments $17o_x$, or by starting at one end and winding $17u_1$ then $17o_1$, then $17u_2$ and so on. At overlap 1102a, filament $17u_1$ comes from the right side going from bottom 1106 to top 1108 of the stent and filament $17o_1$ comes from the left side going from bottom to top, thus overlap 1102a can be said to be a bottom-right-side-filament-under overlap. In overlap 1102b, filament $17u_1$ comes from the left side going from bottom to top of the stent and filament $17o_1$ comes from the right side going from bottom to top, thus overlap 1102b can be said to be a bottom-right-side-filament-over overlap. As shown in FIG. 23, each row 1104a-d has the same type of overlaps throughout the row. Thus, row 1104a has all bottom-right-side-filament-under overlaps 1102a, whereas row 1104b has all bottom-right-side-filament-over overlaps 1102b. Thus, the under-over relationship of the two filament portions at the overlap alternates from row to row from the bottom to the top of the stent. The filament portions that cross over may be portions of the same filament, as described herein below with respect to FIG. 26, or may be portions of two different filaments as shown in FIG. 23.

Figure 24:
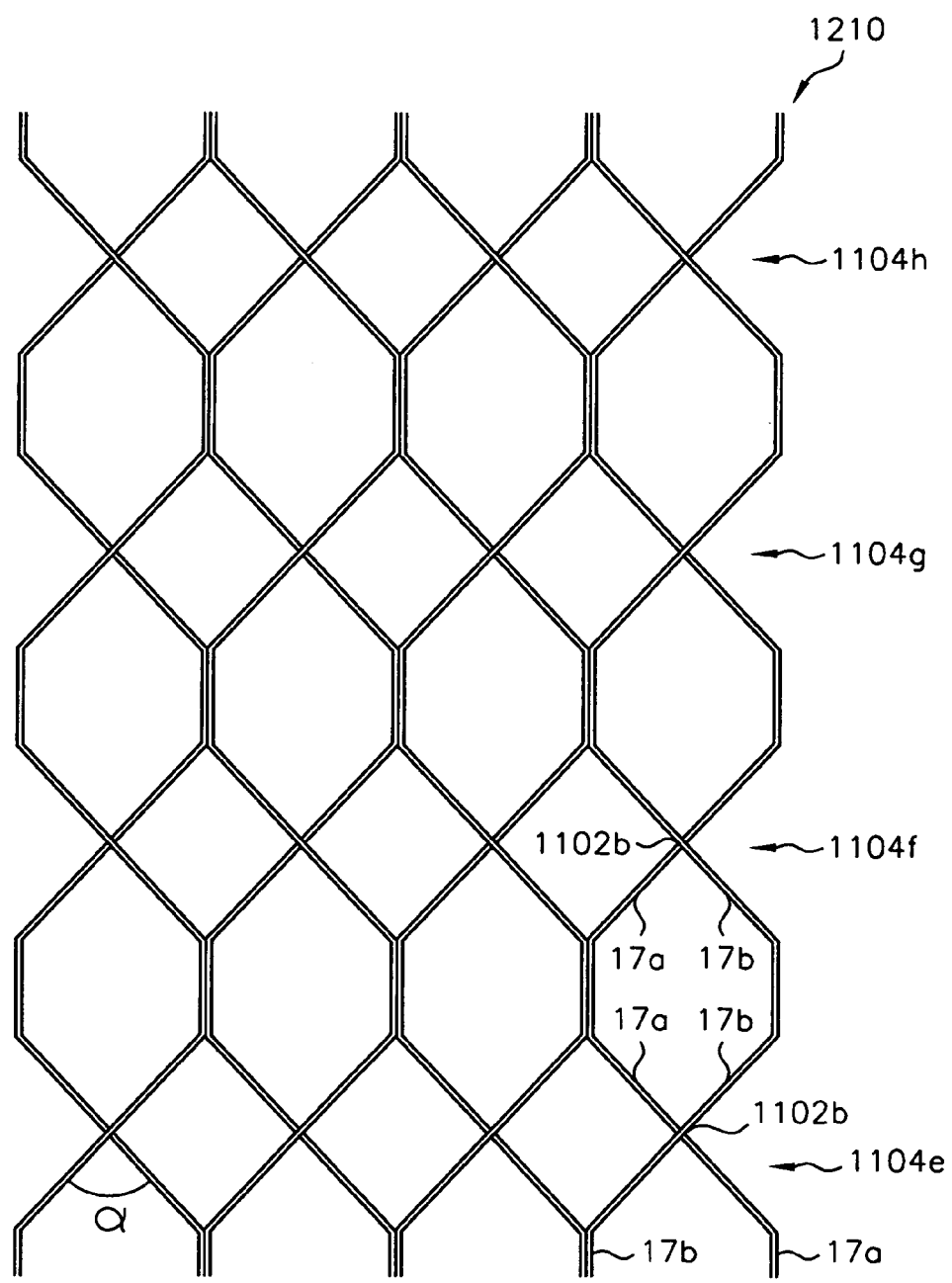
FIG. 24 is an illustration of a portion of an exemplary stent comprising an overlapping polygonal cell architecture from end to end, where the tubular stent has been cut open along a line parallel to the stent axis and flattened, and the under-over relationship is the same for all the overlaps in the stent.

In another embodiment, shown in FIG. 24, the under-over relationship of filaments 17a and 17b of stent 1210 may alternate from row to row moving from the bottom to the top of the stent. For example, filament 17a is positioned over filament 17b to form a bottom-right-side-filament-over overlap 1102b in row 1104e. Filament 17a, now coming from the left in row 1104f, is positioned under filament 17b to again form a bottom-right-side-filament-over overlap 1102b in row 1104f. Thus, in the configuration shown in FIG. 24, all of the overlaps comprise bottom-right-side-filament-over overlaps 1102b. To create such an architecture, the winding preferably progresses from top to bottom or bottom to top either one filament pair 17a and 17b at a time, or winding all pairs 17a and 17b simultaneously such that the overlaps can be laid down without having to tuck one filament under another. Thus, for example, in each row 1104e-h, it is preferable for the filament coming from the bottom left side to be laid down before the filament coming from the bottom right side is laid down so that the overlap can be made easily.

Figure 25:
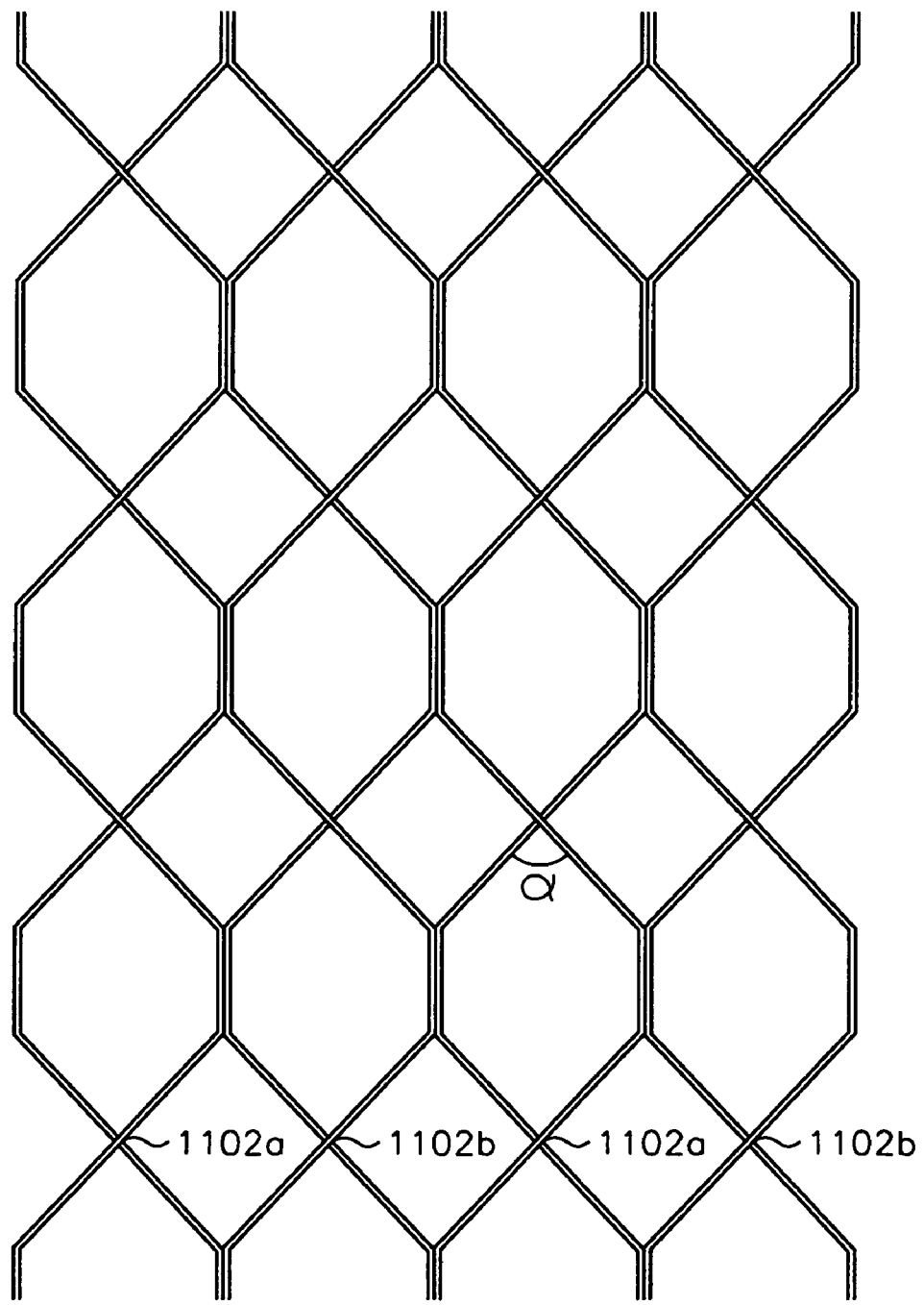
FIG. 25 is an illustration of a portion of an exemplary stent comprising an overlapping polygonal cell architecture from end to end, where the tubular stent has been cut open along a line parallel to the stent axis and flattened, and the under-over relationships of circumferentially adjacent overlaps are opposite to one another.

In yet another embodiment, shown in FIG. 25, the overlapping cell architecture may be created such that overlaps alternate along the circumference of each hoop between bottom-right-side-filament-over overlaps 1102b and bottom-right-side-filament-under overlaps 1102a. Like the embodiment shown in FIG. 24, the embodiment shown in FIG. 25 is also best constructed either by winding adjacent pairs of filaments one pair at a time or by winding all the filaments simultaneously from bottom to top so that each overlap can be laid down without having to tuck any filaments under other filaments a the overlaps.

FIG. 26 shows a stent 1400 wherein each filament 17 extends from bottom 1402 to top 1404 and back to the bottom of the stent again. Thus, the end winding at top 1404 of stent 1400 merely comprises an apex 1406. The end winding at bottom 1402 of stent 1400 comprises a parallel section 1408 of filament ends which may be twisted together, welded, sutured, adhesively bonded, or connected in any way known in the art. As shown in FIG. 26, each filament is wound such that rows 1420a, 1420c, and 1420e comprise bottom-right-side-under overlaps 1102a and rows 1420b and 1420d comprise bottom-right-side-over overlaps 1102b. Circumferentially alternating filaments 17 may be wound in opposite directions, however, so that each row 1420 comprises alternating overlap types 1102a and 1102b. FIG. 26 also shows parallel sections 1408 on the left sides of cells 30. The parallel sections may instead be on the right sides or on alternating sides from one filament to the next circumferentially.

In the embodiments shown in FIGS. 23-25, axial overlap angle α is approximately 90°. In an alternate embodiment, the axial overlap angle may be less than 90° (shown in FIG. 26) or even greater than 90° (not shown). Stents having the architecture shown in FIGS. 23-26 tend to have a lesser shortening ratio than all-braided stents (stents having a braided architecture from end-to-end) of the same length and same axial overlap angle α.

Interspersed Hoops of Zig-Zag Architecture

As shown in FIG. 27, in yet another embodiment 1200 that is particularly beneficial as a balloon-expandable embodiment, one or more rows 1202 comprising zig-zag architecture elements 1204 may be employed between rows 1206 of hexagonal cell architecture elements 1208, preferably in alternating rows. As shown in FIG. 27, a single filament 1210, beginning at end 1211 and ending at end 1212 may be used to wind the entire stent. In the alternative, each column 1214 may be a separate filament, or a single filament may be used to wind multiple columns. The number of rows of zig-zag architecture may be an even number or an odd number. When the number of rows of zig-zag architecture is an odd number and the stent ends are both rows of hexagonal cells, such as shown in FIG. 27, the stent may be well-adapted to being wound with a single filament. When the number of rows of zig-zag architecture is an even number and the stent ends are both rows of hexagonal cells, such as in stent embodiment 1300 of FIG. 28, the stent may be particularly well-adapted to being wound with multiple filaments 1310.

Figure 28:
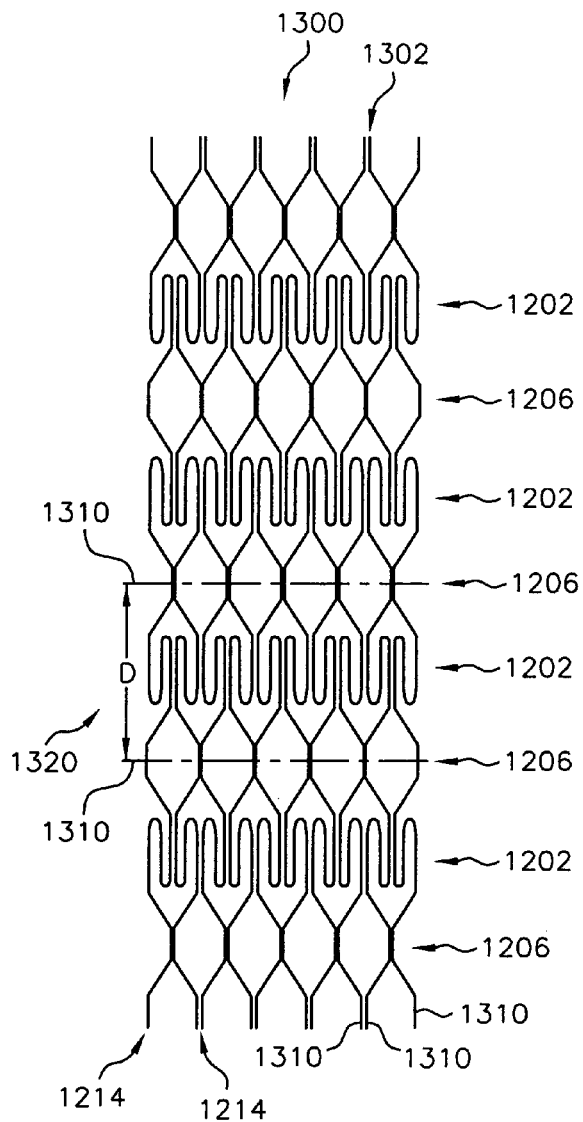
FIG. 28 is an illustration of a portion of an exemplary stent comprising a hybrid polygonal cell and zig-zag architecture having an even number of zig-zag hoops, where the tubular stent has been cut open along a line parallel to the stent axis and flattened.

Although shown in FIG. 28 merely with parallel ends 1302 which may be joined together by soldering, bonding, or any means known in the art, where multiple filaments are used, the end terminations may comprise any of the end terminations known in the art, such as those shown and described herein. The use of rows of zig-zag architecture may be particularly beneficial to reduce the shortening ratio of a stent. The number of rows of zig-zag architecture employed may be varied to provide a desired shortening ratio and/or desired stiffness as compared to designs without rows of zig-zag architecture.

In particular, rows of zig-zag architecture reduce the shortening ratio as compared to rows of overlaps and diamond shaped cells. Thus, for example, distance D between centerlines 1310 of rows 1206 of hexagonal cells in portion 1320 of stent 1300 may change less between expanded and compressed configurations than a comparable portion of a stent having only overlaps and diamond shaped cells between centerlines 1310 separated by the same distance D in a fully expanded state. The distance D in the compressed stated divided by the distance D in the fully expanded state may be referred to as a local shortening ratio. A reduction in the local shortening ratio in any portion of the stent, however, reduces the overall shortening ratio of the stent. Thus, the introduction of one or more portions 1320 into a stent having an overlapping hexagonal cell architecture has the overall effect of reducing the shortening ratio of the stent. The architecture shown in FIGS. 27 and 28 also moves from a compressed configuration to an expanded configuration without any substantial degree of twist, because for each zig-zag element 1204a oriented in a first direction, there is an opposite element 1204b oriented in the opposite direction.

Figure 29:
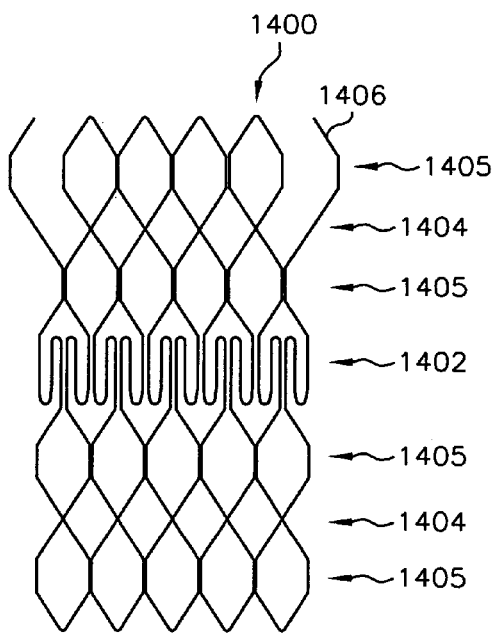
FIG. 29 is an illustration of a portion of an exemplary stent comprising a hybrid overlapping polygonal cell and zig-zag architecture having an odd number of zig-zag hoops and an even number of diamond/overlaplying hoops, where the tubular stent has been cut open along a line parallel to the stent axis and flattened.
Figure 30:
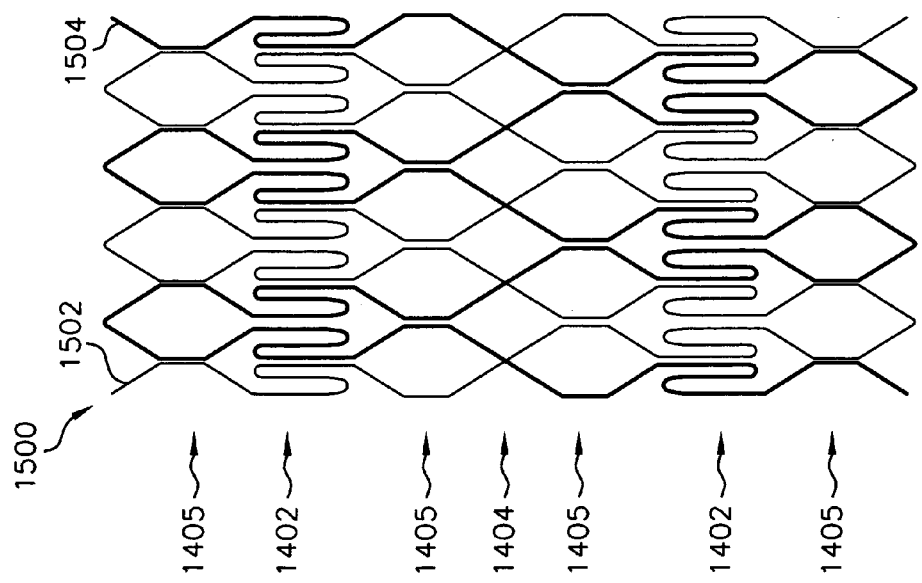
FIG. 30 is an illustration of a portion of an exemplary stent comprising a hybrid overlapping polygonal cell and zig-zag architecture having an even number of zig-zag hoops and an odd number of diamond/overlaplying hoops, where the tubular stent has been cut open along a line parallel to the stent axis and flattened.

One or more zig-zag rows may be combined with the overlapping hexagonal cell architecture, as shown in FIGS. 29 and 30. As illustrated by stent 1400 in FIG. 29, a single row 1402 (or an odd number of rows) of zig-zag architecture combined with an even number of diamond/overlap rows 1404 between hexagonal cell rows 1405 may allow a single filament 1406 to be used to wind the stent. Even in an embodiment having an odd number of diamond/overlap rows (not shown) and an odd number of zig-zag rows, the stent may be wound with a single filament. As illustrated by stent 1500 in FIG. 30, an even number of rows 1402 of zig-zag architecture combined with an odd number of diamond/overlap rows 1404 may allow the stent to be wound using only two filaments 1502 and 1504 (highlighted in dark). As illustrated by stent 1600 in FIG. 31, an even number of rows 1402 of zig-zag architecture combined with an even number of diamond/overlap rows 1404 lends itself well to the use of multiple filaments, one for each traversal from end 1602 to end 1604, or one for each traversal from end 1602 to end 1604 and back to end 1602, as illustrated by highlighted filament 1606. Any combination of zig-zag architecture, hexagonal cell architecture, and overlapping hexagonal cell architecture may be provided, however, with even or odd numbers of row and single or multiple filaments as desired. Even where the design generally lends itself well to using multiple filaments, a single filament may be used, depending on the type of end winding chosen. The designs shown herein are merely exemplary, and not limiting of the invention.

Any of the various architectures described herein and any of the end-windings shown herein may be combined as desired. The size of the hexagonal and diamond-shaped cells may be any size and the size may vary along the length of the stent to provide specific advantages. The methods of constructing the various braided and wound stent architectures are well known in the art. For example, the method for constructing the polygonal cell stent architecture is described in U.S. Pat. No. 5,540,712 to Kleshinski et al. and essentially comprises winding the stent around pins on a mandrel.

Figure 31:
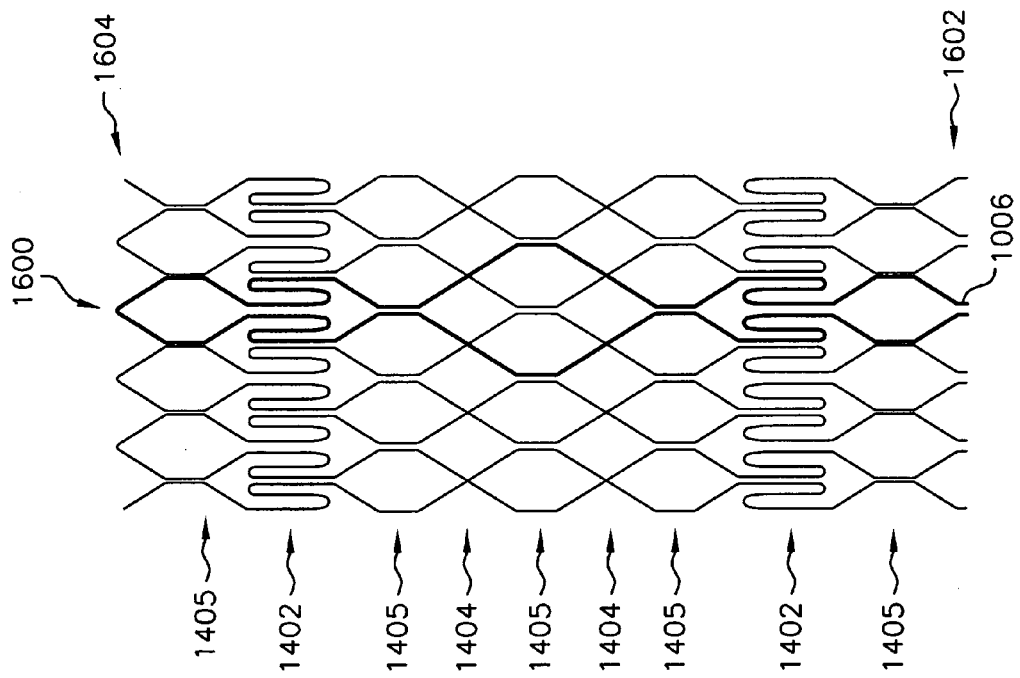
FIG. 31 is an illustration of a portion of an exemplary stent comprising a hybrid overlapping polygonal cell and zig-zag architecture having an even number of zig-zag hoops and an even number of diamond/overlaplying hoops, where the tubular stent has been cut open along a line parallel to the stent axis and flattened.

The overlapping hexagonal cell architecture shown in FIGS. 23-26 as well as the interspersed hoops of zig-zag architecture between hexagonal cells, as shown in FIGS. 27 and 28, or between overlapping hexagonal cells, as shown in FIGS. 29-31, have some commonality. Both may be described as comprising a set of one or more filaments in a repeating configuration having at least one bent portion, wherein the repeating configuration defines at least a first hoop comprising hexagonal cells, the first hoop being axially adjacent to a second hoop that does not comprise hexagonal cells. This same description also pertains to the architectures shown in FIGS. 3, 6, 8-16, and 19-22 and described herein.

Overlapping Zig-Zag Architecture

Figure 32:
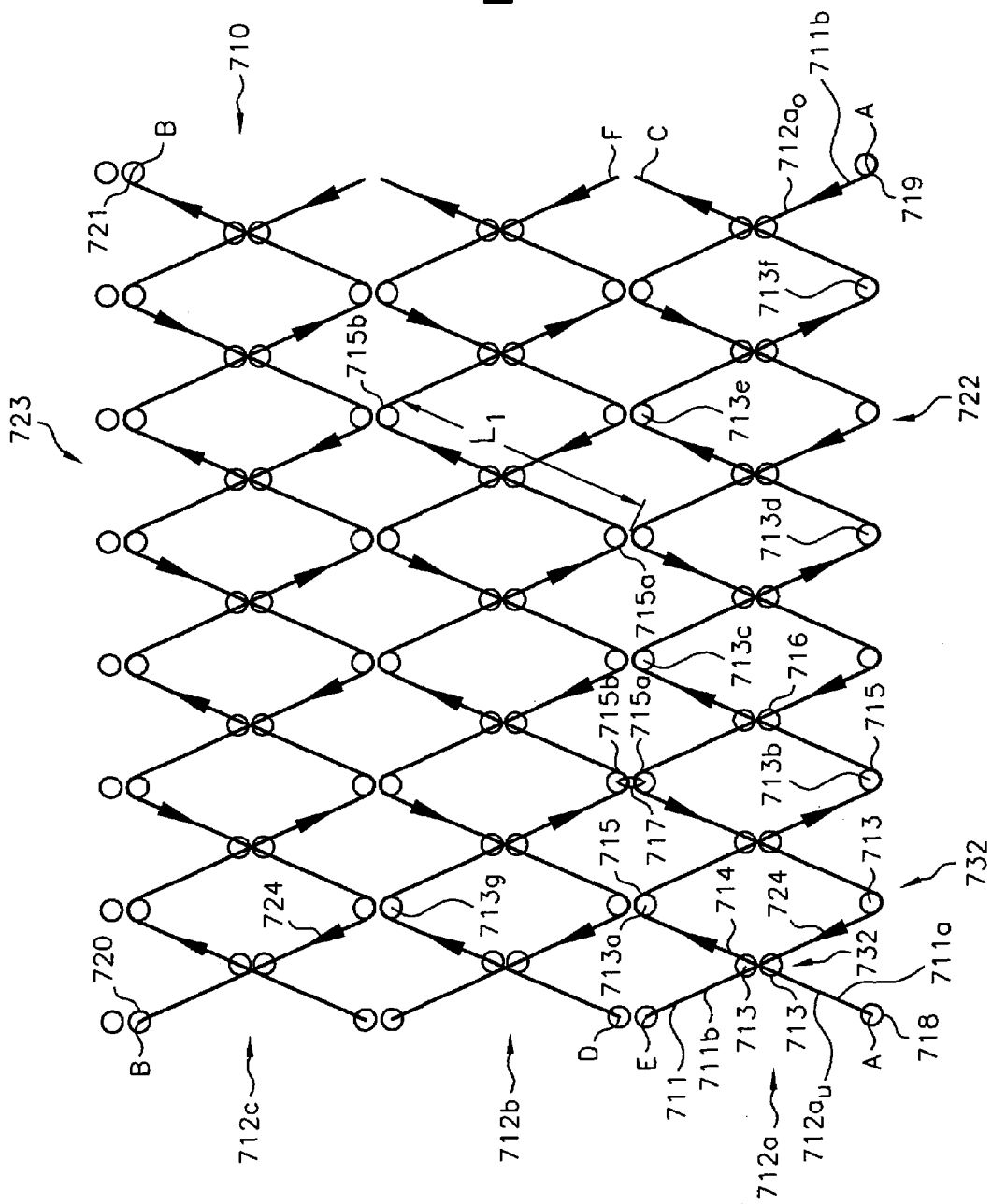
FIG. 32 is an illustration of a portion of an exemplary stent comprising an overlapping zig-zag architecture, where the tubular stent has been cut open along a line parallel to the stent axis and flattened.

Overlapping zig-zag architecture, in addition to being useful as an end winding for the termination of a stent comprising multiple filaments such as for braided or hexagonal cell architectures or hybrids thereof, as shown and described with respect to FIGS. 9 and 21, may also be beneficial for use throughout the length of an entire stent. FIG. 32 illustrates an exemplary stent 710 according to the present invention. Stent 710 is generally cylindrical and adapted to be inserted into a lumen. Stent 710 has been cut longitudinally and laid flat for purposes of illustration. Stent 710 is formed by winding a continuous filament 711, such as a wire, into a zig-zag or sinusoidal configuration and into a plurality of circumferential hoop pairs 712a, 712b, 712c disposed in succession along the length of stent 710. Each hoop pair comprises an "underlying hoop," such as hoop $712a_u$ and an "overlying hoop," such as hoop $712a_o$ that overlaps the underlying hoop and is 180° out of phase with the underlying hoop.

Filament 711 is preferably a nitinol wire, which provides a stent that auto-expands by shape memory, but it may be made of any suitable material, including stainless steel and thermoplastic polymers. Thus, the stent may be capable of deployment by shape memory auto-expansion, thermal auto-expansion or balloon expansion, as are well-known in the art. The width of the filament affects the radial force exerted by stent 710. Increasing the diameter of filament 711 increases the radial force. The stent may comprise a single filament, a pair of filaments, such as filaments 711a and 711b shown in FIG. 32, or a plurality of filaments. For example, each hoop pair or hoop component (underlying hoop or overlying hoop) may each comprise a distinct filament.

For convenience, the configuration of the wound filament is referred to throughout having a "zig-zag" shape with zigs or zig lengths. As so used herein, however, the term "zig-zag" encompasses not only a jagged zig-zag shape where the apex sections are relatively sharp and the struts are substantially straight, but also a sinusoidal shape where the apex sections are rounded and, together with the struts, form a shape resembling a sine wave having an amplitude and a period or wavelength. Similarly, although the apex sections may be referred to as defining a zig angle, the angle may be more rounded such that lesser and greater angles may be more envisioned as smaller and larger radii of curvature, respectively. Of course, the actual filament configuration may have a shape intermediate the jagged zig-zag and rounded sine wave shapes, or may be even more rounded than a sine wave, and the apex sections may in fact have a truncated, straight edge rather than a rounded shape or sharp angle, as described herein later.

One advantage of providing overlaps instead of apex sections, is that each overlap eliminates a pair of abutting apex sections that may need to be sutured or otherwise connected together. This simplifies and decreases the cost of manufacturing, and eliminates the number of sites where apex sections would otherwise slide over one another. The overlapping zig-zags create a potentially more flexible stent without sacrificing kink-resistance. The overlapping zig-zag design may be particularly well-suited for end winding applications where greater radial strength may be required.

To form stent 710, filament 711 is wound around pins 713 on a mandrel (not shown). The mandrel is typically cylindrical (although other shapes may be used as necessary to form stents of varying shapes) and of a diameter determined by the diameter of the vessel into which stent 710 is to be inserted. Typically, the mandrel diameter, and hence the intended diameter of stent 710, is slightly larger (for example, by one millimeter) than the diameter of the vessel. The length of stent 710 is also determined by the particular application. As illustrated in the figures herein, the stents are shown cut longitudinally and flattened, and the pins around which the stents are formed are also shown correspondingly. It should be understood that the left hand side of the stent in each figure as shown is continuous with the right hand side of the stent when in a tubular form. Thus, for example, point A in FIG. 32 (at the bottom of the stent) is shown on both the left and right hand side in the figure, but comprises only a single point. Point B (at the top of the stent) is similarly shown.

Stent 710 is formed by winding filament 711a around pins 713 beginning at point A in FIG. 32. Filament 711a is first wound around pins 713a, 713b, 713c and so forth in accordance with arrows 724 (which are provided for illustrative purposes only) until reaching pin 713f, as shown. In this manner, zig-zag members are formed and defined by a successive series of substantially straight sections (struts) 714 connected by apex sections 715 alternately pointing in opposite axial directions. The winding continues in this manner around the mandrel until a first hoop 712a is completed by winding filament 711 completely around the circumference of the mandrel. Once underlying hoop $712a_u$ is formed, filament 711a is extended from pin 713f to and around pin 713g.

Winding then continues as before to form a second underlying hoop $712b_u$ adjacent to first underlying hoop $712a_u$. By forming hoops in this manner, adjacent hoops $712a_u$ and $712b_u$ are connected in part by the portion of filament 711a connecting point C to point D extending between hoop $712a_u$ and hoop $712b_u$. At the completion of the hoop $712b_u$, filament 711a is again extended to the hoop $712c_u$, which is wound as hoops $712a_u$ and $712b_u$.

Next, filament 711b is wound to form hoop $712a_o$. Hoop $712a_o$ is formed over top of and out of phase with hoop $712a_u$. Thus, overlying hoop $712a_o$ crosses over underlying hoop $712a_u$ at a plurality of overlaps 716. Overlying hoops $712b_o$ and $712c_o$ are then constructed in the same way as $712a_o$, with hoops $712a_o$-$712c_o$ having a similar relationship to one another as hoops $712a_u$-$712c_u$. Although stent 710 comprises three overlapping hoop pairs, the stent may comprise any number of overlapping hoop pairs. Thus, as shown in FIG. 32, the stent comprises N overlapping hoop pairs, comprising filaments 711a and 711b, each beginning at point A and ending at point B, but traversing the stent in opposite circumferential directions. Ends 718 and 719 and ends 720 and 721 of filaments 711a and 711b, respectively, may be joined together by any means known in the art, such as but not limited to, twisting them together, welding, adhesive bonding, or brazing, and may extend parallel adjacent to one another for some distance to facilitate such connection.

In an alternative embodiment, rather than having a plurality of filaments 711a and 711b, stent 710 may comprise only a single filament 711 comprising a first portion 711a and a second portion 711b. In such case, end 720 of filament 711b and end 721 of filament 711a are not ends at all, but rather are connected to one another at approximately a center point of single filament 711. Filament 711 thus begins at end 718 and extends from point A in hoop pair 712a of stent 710 to hoop pair 712c and back again to hoop pair 712a to end 719 at point A. In such case, winding of portion 711b proceeds in the opposite direction than indicated by arrows 724 corresponding to portion 711b. Alternatively, the winding direction of portion 711a can be reversed. In yet another embodiment, filament 711a, instead of being connected between point C and point D, is connected at point C to point F, and filament 711b is connected at point E to point D. Thus, the apex created at the junction of points C and F may be attached to the apex created at the junction of points D and E, with a connecting member, such as a suture.

In yet another alternate embodiment, each hoop pair may comprise a single wire. Thus, hoop pair 712a may comprise portion 711a which extends from end 718 at point A to point C that connects to point E of portion 711b, in which case the winding on portion 711b in hoop pair 712a proceeds opposite arrows 724 shown thereon, and the filament ends at end 719. Alternatively, the winding direction of portion 711a can be reversed while the winding direction of portion 711a remains as indicated by the arrows. Ends 718 and 719 may be connected by any means known in the art. In this embodiment, hoop pair 712b comprises another filament beginning and ending at points D and F. Each adjacent set of hoop pairs (712a and 712b, for example) has at least one pair of abutting apex sections 715a and 715b which may be attached to one another by any other suitable attachment means 717 known in the art, including without limitation, tying, suturing, gluing, and stapling, with the glue or sutures being absorbable or non-absorbable, and including the use of polymer-containing connections. Preferably, each pair of abutting apex sections is attached together.

As shown in FIG. 32, there are fourteen columns 732 of pins 713, which is an even number that is not divisible by 4

Figure 33:
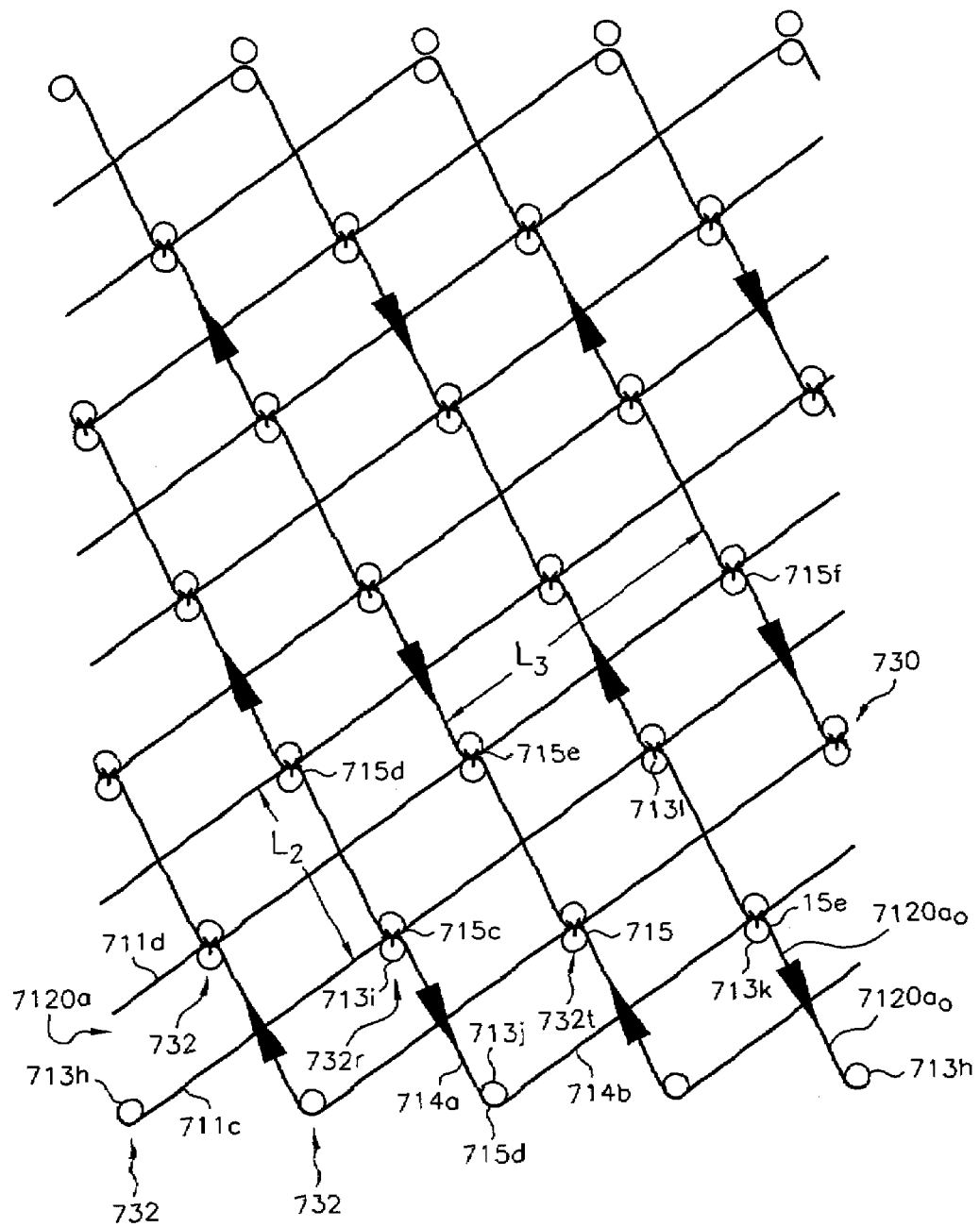
FIG. 33 is an illustration of a portion of an exemplary stent comprising an overlapping zig-zag architecture having struts of different lengths and wound on a mandrel having a number of pin columns divisible by 4, where the tubular stent has been cut open along a line parallel to the stent axis and flattened.

(without a remainder). If, instead, there are only twelve columns 732 (or any number of columns that is divisible by 4), each underlying hoop and each overlying hoop may be created with a distinct wire. FIG. 33 illustrates this concept and also illustrates another variation wherein each apex section 715 connects struts having different lengths. Unlike the embodiment shown in FIG. 32, wherein each strut 714 has an equal length L1, FIG. 33 illustrates an embodiment comprising struts 714a having a relatively short length L2 and struts 714b having a relatively long length L3. Strut lengths L1, L2, and L3 denote the distances between connected apex sections 715a and 715b, 715c and 715d, and 715d to 715e, respectively, as measured along the strut.

FIG. 33 also shows the pattern present when the mandrel has an even number of columns divisible by 4. As shown, wire 711c may be wound from the end pin 713h to pin 713i, back to end pin 713j and so on, until reaching pin 713h again. Thus, a single filament 711c may be used to create underlying hoop $7120a_u$ and an additional filament 711d may be used to create overlying hoop $7120a_o$. Each hoop pair may thus comprise multiple filaments. The ends of each filament may be connected together by any means known in the art.

Figure 34:
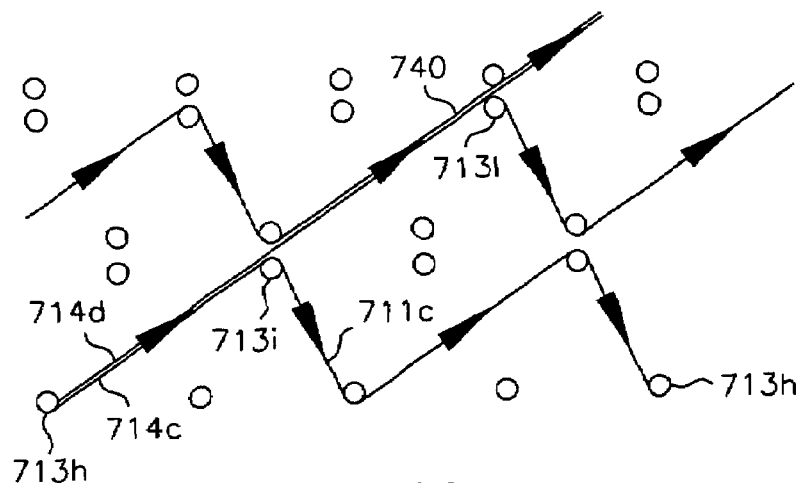
FIG. 34 is an illustration of a fabrication method for an underlying hoop portion of an exemplary stent comprising an overlapping zig-zag architecture having struts of different lengths being wound on a mandrel having a number of pin columns divisible by 4, where the portion has been cut open along a line parallel to the stent axis and flattened.

Rather than forming each overlying hoop and each underlying hoop using distinct filaments, the winding of filament 711c may continue around pin 713h again, as shown in FIG. 34. This winding pattern creates a second strut 714d parallel to first strut 714c between pins 713h and 713i and then extending onward to pin 713l, and then winding back and forth to form an adjacent hoop. This pattern produces a stent having at least one helical spine 740 comprising the aligned parallel struts (such as struts 714c and 714d) created in each hoop. Where two filaments are used, one to form the underlying hoops and one to form the overlying hoops, two helical spines are present, one traversing the circumference of the stent in a clockwise manner from bottom to top of the stent, and the other traversing the circumference of the stent in a counter-clockwise manner from the bottom to top of the stent, the spines crossing over each other in at least one location. Even where a single filament is used, the helical spine essentially traverses the stent from bottom to top to bottom again traversing in a single helical direction, but which still crosses over itself in at least one location.

Figure 35:
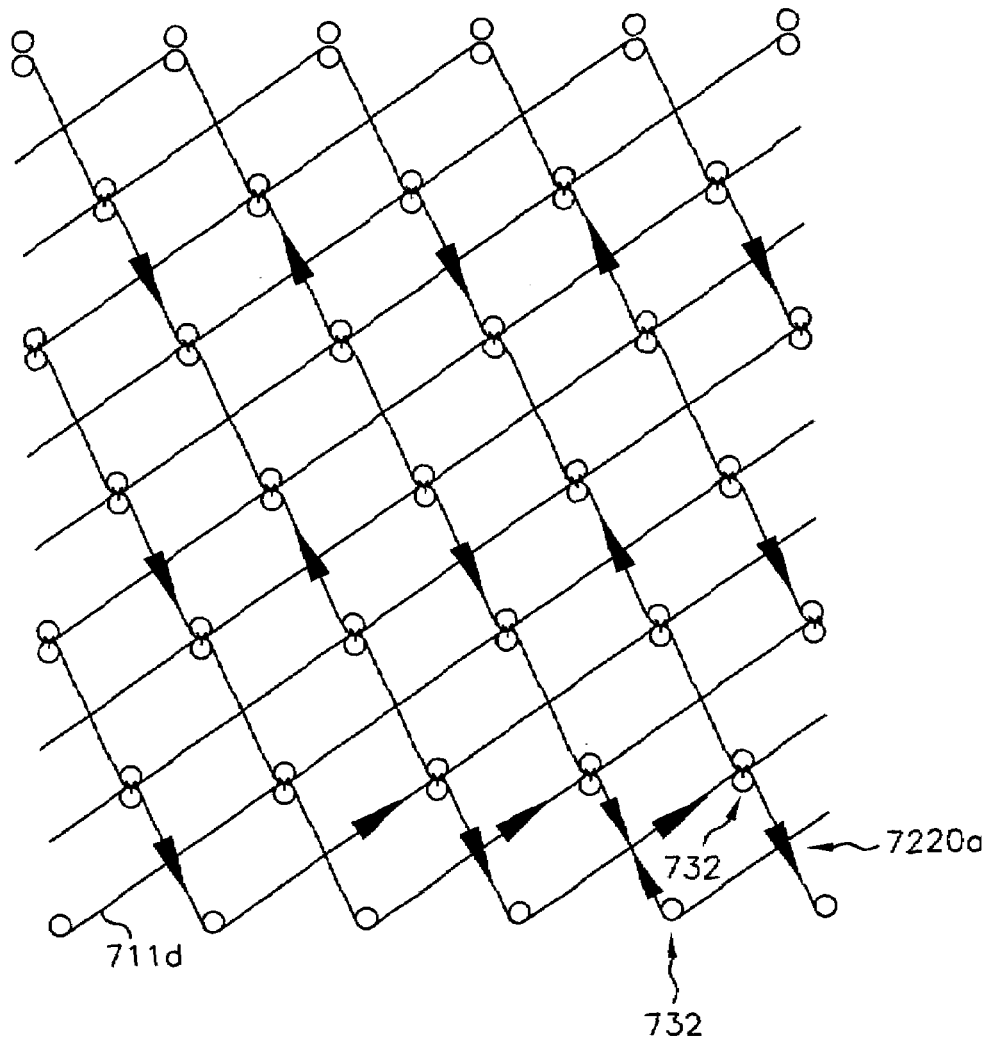
FIG. 35 is an illustration of a portion of an exemplary stent comprising an overlapping zig-zag architecture having struts of different lengths and wound on a mandrel having a number of pin columns not divisible by 4, where the tubular stent has been cut open along a line parallel to the stent axis and flattened.
Figure 36:
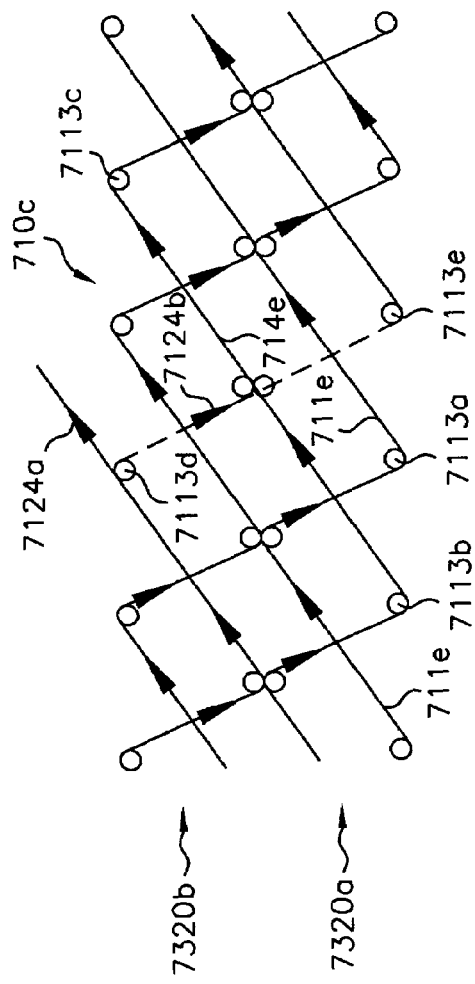
FIG. 36 is an illustration of a fabrication method for a portion of an exemplary stent comprising an overlapping zig-zag architecture having struts of different lengths being wound on a mandrel having a number of pin columns not divisible by 4, where the tubular stent has been cut open along a line parallel to the stent axis and flattened.

In contrast to FIGS. 33 and 34, and similar to FIG. 32, FIG. 35 depicts a mandrel having an even number of pin columns 732 that is not divisible by 4. Thus, as with the design shown in FIG. 32, a single filament 711d may be used to create hoop pair 7220a. As shown in FIG. 36, a single filament 711e may instead be used to wind the entire stent 710c. In such manner, filament 711e starts at pin 7113a and forms hoop pair 7320a by making two traversals around the mandrel until reaching pin 7113b. From pin 7113b, the filament is then extended to pin 7113c, forming an extra long strut 714e, from which point the filament winds back and forth to create hoop pair 7320b. When reaching pin 7113d, filament 711e may continue on to another axially adjacent row as shown by solid line marked with arrow 7124a, or upon reaching a designated pin in an end row of pins, can be wound back to pin 7113e along the dashed line marked by arrow 7124b. This option of winding each hoop pair and then extending helically to wind an adjacent hoop pair until reaching the end of an Nth hoop pair, and then extending helically back to the opposite end row may also be practiced with respect to the equal-strut length winding pattern shown in FIG. 32. The portion of filament 711e that extends along arrow 7124b as illustrated by the dashed line from pin 7113d at one end of the stent to pin 7113e at the other end may be woven alternately over and under each strut that it crosses, creating a series of overlaps and underlaps to further bind the stent structure together.

It should be noted that the stent architectures depicted herein may be combined with one another. That is, a stent may comprise a first longitudinal section having the configuration shown in FIG. 32 whereas a second longitudinal section may have the configuration shown in FIG. 33. Also, although overlapping zig-zag designs are shown herein fabricated using a particular mandrel pin design, other mandrel pin designs may be utilized, including designs which may be used to provide stents having a first cell size in a first longitudinal portion and a second cell size in a second longitudinal portion using the same winding scheme.

Figure 37:
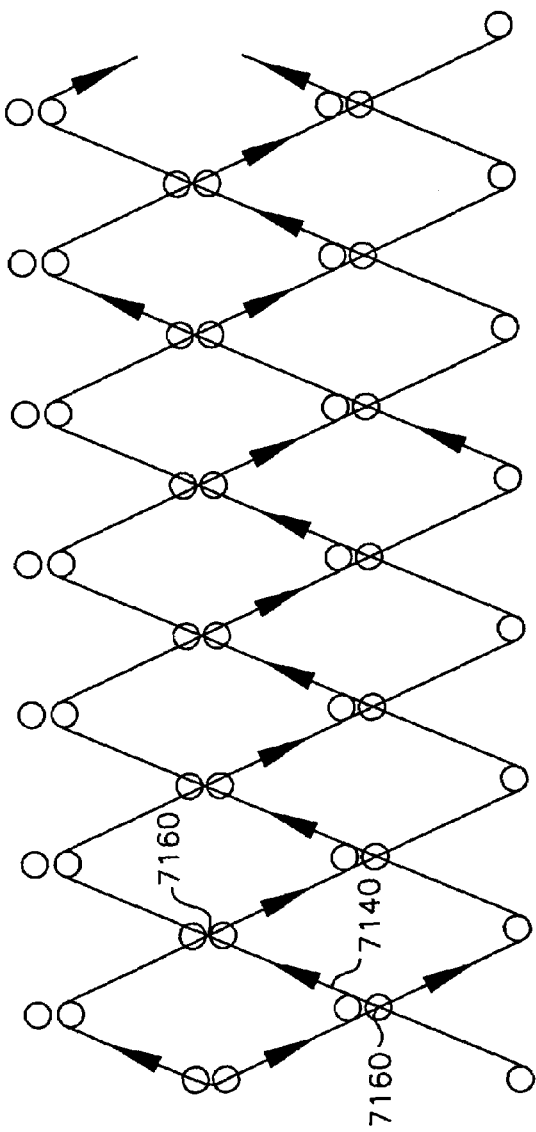
FIG. 37 is an illustration of a portion of an exemplary stent comprising an overlapping zig-zag architecture where each strut comprises multiple overlaps, where the tubular stent has been cut open along a line parallel to the stent axis and flattened.

Finally, although shown in FIGS. 32-36 each strut only has a single overlap, in an alternate embodiment, such as shown in FIG. 37, each strut 7140 may have multiple overlaps 7160 along its length. For each increase in the number of overlaps per strut, the number of apex sections is reduced. Reducing the number of apex sections further reduces the number of sutures needed to connect abutting apex sections.

Any of the variations described herein may be combined with any other variation described herein or known in the art, where practical, to develop a stent architecture according to the present invention. Moreover, the "struts" of each apex section and the connections therebetween may be straight, as in a jagged zig-zag configuration, or curved somewhat, such as when the overall stent section is more sinusoidal.

Methods of Treating a Body Lumen

Figure 22:
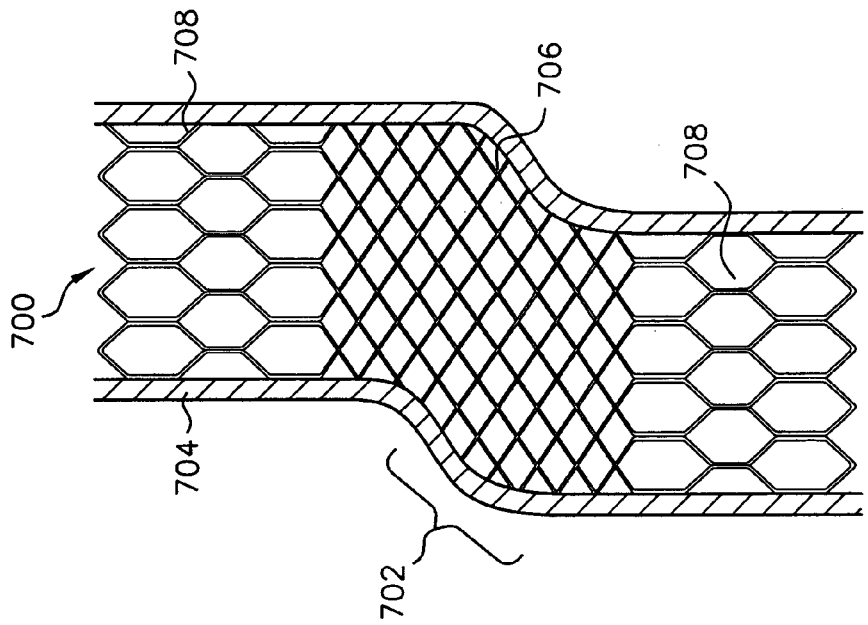
FIG. 22 is an illustration of a portion of a stent embodiment of the present invention shown implanted in a lumen having a tortuous region, the lumen shown in cross-section.

In addition to the various structures disclosed herein, the invention also comprises methods for treating a body lumen, the method comprising implanting any one of the stent structures described herein. In particular, one treatment method may comprise implanting one of the structures described herein with a higher-radial-strength segment at one or both ends of the stent, especially on the upstream end of the stent, as is shown in FIG. 10. Another treatment method may comprise implanting a more flexible region aligned with a tortuous region of a lumen as shown in FIG. 22. Another treatment method may comprise implanting a stent according to this invention from a compressed to an extended configuration without imparting a twisting motion to the stent. Yet another method may comprise implanting a segment having a greater percentage of open area adjacent to a region of the lumen having intersecting lumen, as is shown in FIG. 20. Finally, the invention also comprises a method of counteracting an end effect of a braided stent by incorporating a wound section onto the end of the braided stent, as described herein.

The method may also comprise deploying a plastically deformable stent, particularly one comprising an architecture such as is shown in FIGS. 23-31, by inflating a balloon to expand the stent. The method of inflating a balloon to deploy a stent is generally known in the art. Implanting a stent according to this invention may comprise expanding the stent from a compressed to an extended configuration without imparting a twisting motion to the stent, in particular when the stent has no zig-zag end winding, or has the overlapping zig-zag end winding shown in FIG. 21.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A stent comprising at least one portion comprising a plurality of zig-zag or sinusoidal filaments defined by a successive series of three struts connected to one another by a pair of adjacent apex sections pointing in opposite axial directions, at least a first zig-zag filament and contacted second zig-zag filament and out of phase with the second zig-zag filament to form an overlap between at least one strut of the first zig-zag filament and one strut of the second zig-zag filament, wherein each filament comprises a distinct, individually-formed wire or polymer member, not a portion of slotted metal or cut or etched tubing, and at least one continuous filament extends into both a wound section and a braided section.

2. The stent of claim 1, wherein each zig-zag member comprises a different filament.

3. The stent of claim 1, wherein the stent comprises a tubular stent having a tubular axis having a length, said stent comprising a plurality of axially overlapping hoop pairs axially disposed in succession along the length of said axis, each hoop pair comprising an underlying hoop comprising a plurality of said first zig-zag members and an overlying hoop comprising a plurality of said second zig-zag members, the underlying hoop and overlying hoop forming a plurality of said overlaps.

4. The stent of claim 3, wherein at least a first plurality of apex sections each connect a strut having a first strut length to a strut having a second strut length.

5. The stent of claim 3, wherein at least a first plurality of apex sections each connect two struts having a same strut length.

6. The stent of claim 3, wherein facing apex sections of axially adjacent hoops abut one another and at least one pair of abutting apex sections of adjacent hoops are connected to one another by a connecting member.

7. The stent of claim 6, wherein the connecting member comprises an absorbable or non-absorbable suture, an absorbable or non-absorbable adhesive bond, or a staple.

8. The stent of claim 1, having an axis with a length and comprising a plurality of axially overlapping hoop pairs axially disposed in succession along the length of the axis.

9. The stent of claim 1, wherein the at least one continuous filament comprises a material selected from the group consisting of: nitinol, stainless steel, and a thermoplastic polymer.

10. The stent of claim 9, wherein the stent consists of a single continuous filament.

11. The stent of claim 9, wherein the stent comprises a plurality of continuous filaments.

12. The stent of claim 1 further comprising at least one helical spine.

13. The stent of claim 1, wherein the at least one portion comprises an end winding.

14. The stent of claim 1, wherein the at least one portion comprises an entire stent.

15. A stent comprising at least one section comprising a set of one or more filaments in a repeating configuration having at least one bent portion, wherein the repeating configuration defines at least a first hoop comprising hexagonal cells axially adjacent to a second hoop that does not comprise hexagonal cells, wherein each filament comprises a distinct, individually-formed wire or polymer member, not a portion of slotted metal or cut or etched tubing, and at least one continuous filament extends into both a wound section and a braided section, wherein said at least one continuous filament is the same filament in both said wound section and said braided section.

16. The stent of claim 15, wherein the section comprises an end winding comprising a zig-zag configuration.

17. The stent of claim 16, wherein the zig-zag configuration of the end winding comprises an overlapping zig-zag configuration.

18. The stent of claim 17, wherein the overlapping zig-zag configuration comprises sets of double filaments extending parallel to one another.

19. The stent of claim 17, wherein the overlapping zig-zag configuration comprises sets of double filaments intersecting one another.

20. The stent of claim 15, wherein the section has a radially compressed configuration and a radially expanded configuration, and in which both the first stent architecture and the second stent architecture comprise architectures having substantially no degree of twist between the compressed and expanded configurations.

21. The stent of claim 15, wherein the section has a radially compressed configuration and a radially expanded configuration, and is self-expandable from the radially compressed configuration to the radially expanded configuration by spring elasticity or by thermal or stress-induced return of a shape memory material.

22. The stent of claim 15, wherein the section has a radially compressed configuration and a radially expanded configuration, and is balloon-expandable from the radially compressed configuration to the radially expanded configuration.

23. The stent of claim 15, wherein the stent comprises a plurality of first hoops comprising hexagonally-shaped cells and one or more second hoops comprising diamond-shaped cells and crossovers, the first hoops and second hoops arranged in an axially alternating series.

24. The stent of claim 23, wherein the stent has a first end and a second end, and the axially alternating series extends from the first end of the stent to the second end of the stent.

25. The stent of claim 15, wherein the stent comprises plastically deformable materials of construction, the plastically deformable materials selected from the group consisting of: gold, platinum, tantalum, titanium, stainless steel, tungsten, palladium, a nickel alloy, a titanium alloy, a cobalt alloy, and a combination thereof.

26. The stent of claim 15, wherein the second hoop comprises a plurality of diamond-shaped cells and a plurality of crossovers.

27. The stent of claim 15, wherein the stent comprises a plurality of filaments, each filament extending from a first end of the stent to a second end of the stent and then back to the first end of the stent.

28. The stent of claim 15, wherein the stent has a radially compressed configuration, a radially expanded configuration, an axial crossover angle, a first length in the compressed configuration, a second length in the expanded configuration, and a shortening ratio comprising the first length divided by the second length, in which the shortening ratio is less than for an all-braided stent having the same first length and a same axial crossover angle.

29. The stent of claim 15 wherein the second hoop comprises a zig-zag architecture.

30. The stent of claim 15 wherein the stent comprises a plurality of filaments.

31. The stent of claim 15 wherein the stent consists of a single filament.

32. The stent of claim 15 wherein the repeating configuration further defines a third hoop that does not comprise hexagonal cells axially adjacent to a first hoop, the third hoop and the second hoop having different architectures.

33. The stent of claim 32 wherein the second hoop comprises a plurality of diamond-shaped cells and a plurality of crossovers and the third hoop comprises a zig-zag architecture.

34. A multi-section stent comprising at least one braided section, which comprises a cylindrical mesh of a first set of filaments, and at least one wound section, which is connected to said braided section and comprises a second set of one or more filaments in a repeating configuration having at least one bent portion, wherein the repeating configuration defines an overlapping zig-zag configuration or a configuration having overlapping hexagonal cells, wherein each filament comprises a distinct, individually-formed wire or polymer member, not a portion of slotted metal or cut or etched tubing, and at least one continuous filament extends into both the wound section and the braided section, wherein said at least one continuous filament is the same filament in both said wound section and said braided section.

35. A multi-section filamentary stent comprising:
a first section, having a first stent architecture comprising one or more filaments in a first geometric configuration, the first stent architecture having a first flexibility and a first radial force, and
a second section, having a second stent architecture comprising one or more filaments in a second geometric configuration, the second stent architecture having a second flexibility less than the first flexibility and a second radial strength greater than the first radial strength;
wherein the stent comprises at least one continuous filament contained in both the first and second sections, the first stent architecture comprises a braided stent architecture, and the second stent architecture comprises an overlapping zig-zag configuration or a configuration having overlapping hexagonal cells, wherein each filament comprises a distinct, individually-formed wire or polymer member, not a portion of slotted metal or cut or etched tubing, and at least one continuous filament extends into both the first section and the second section, wherein said at least one continuous filament is the same filament in both said first section and said second section.

36. A multi-section filamentary stent comprising:
a first section, having a first stent architecture comprising one or more filaments in a first geometric configuration, the first stent architecture having a first flexibility and a first radial force, and
a second section, having a second stent architecture comprising one or more filaments in a second geometric configuration, the second stent architecture having a second flexibility less than the first flexibility and a second radial strength greater than the first radial strength;
wherein the stent comprises at least one continuous filament contained in both the first and second sections, the first stent architecture comprises a braided stent architecture, and the second stent architecture comprises an overlapping zig-zag configuration or a configuration having overlapping hexagonal cells, wherein each filament comprises a distinct, individually-formed wire or polymer member, not a portion of slotted metal or cut or etched tubing, and at least one continuous filament extends into both the first section and the second section, wherein the second stent geometric configuration defines a plurality of polygonal cells having as sides thereof straight axially-extending portions joined together along a set of parallel segments, the parallel segments deviating from one another proximally and distally of each parallel segment into diagonal segments, such that each set of parallel segments and attached diagonal segments form a Y-shaped intersection, each Y-shaped intersection at an interface between the first section and the second section having diagonal segments that extend into the first section.

37. The stent of claim 36 wherein the second stent geometric configuration further comprises an end winding having the overlapping zig-zag configuration or the configuration having overlapping hexagonal cells.

38. The stent of claim 36 wherein the second stent geometric configuration further comprises an end winding having the overlapping zig-zag configuration with sets of double filaments extending parallel to one another.

39. The stent of claim 36 wherein the second stent geometric configuration further comprises an end winding having the overlapping zig-zag configuration with sets of double filaments intersecting one another.

* * * * *